United States Patent
Deaton et al.

(10) Patent No.: US 9,040,170 B2
(45) Date of Patent: May 26, 2015

(54) ELECTROLUMINESCENT DEVICE WITH QUINAZOLINE COMPLEX EMITTER

(75) Inventors: Joseph C. Deaton, Rochester, NY (US); Barbara B. Lussier, Rochester, NY (US)

(73) Assignee: Global OLED Technology LLC, Herndon, VA (US)

(*) Notice: Subject to any disclaimer, the term of this patent is extended or adjusted under 35 U.S.C. 154(b) by 1840 days.

(21) Appl. No.: 11/289,023

(22) Filed: Nov. 29, 2005

(65) Prior Publication Data

US 2007/0122655 A1    May 31, 2007

(51) Int. Cl.
| | |
|---|---|
| H01L 51/54 | (2006.01) |
| C09K 11/06 | (2006.01) |
| H01L 51/00 | (2006.01) |
| H05B 33/14 | (2006.01) |
| H01L 51/50 | (2006.01) |

(52) U.S. Cl.
CPC ............ *C09K 11/06* (2013.01); *H01L 51/0085* (2013.01); *H01L 51/5016* (2013.01); *C09K 2211/1044* (2013.01); *C09K 2211/185* (2013.01); *H05B 33/14* (2013.01)

(58) Field of Classification Search
None
See application file for complete search history.

(56) References Cited

U.S. PATENT DOCUMENTS

| | | |
|---|---|---|
| 3,172,862 A | 3/1965 | Gurnee et al. |
| 3,173,050 A | 3/1965 | Gurnee et al. |
| 3,180,730 A | 4/1965 | Klupfel et al. |
| 3,567,450 A | 3/1971 | Brantly et al. |
| 3,658,520 A | 4/1972 | Brantly et al. |
| 3,710,167 A | 1/1973 | Dresner et al. |
| 4,356,429 A | 10/1982 | Tang |
| 4,539,507 A | 9/1985 | VanSlyke et al. |
| 4,720,432 A | 1/1988 | VanSlyke et al. |
| 4,768,292 A | 9/1988 | Manzei |
| 4,769,292 A | 9/1988 | Tang et al. |
| 4,885,211 A | 12/1989 | Tang et al. |
| 4,885,221 A | 12/1989 | Tsuneeda |
| 5,059,861 A | 10/1991 | Littman et al. |
| 5,059,862 A | 10/1991 | VanSlyke et al. |
| 5,061,569 A | 10/1991 | VanSlyke et al. |
| 5,121,029 A | 6/1992 | Hosokawa et al. |
| 5,141,671 A | 8/1992 | Bryan et al. |
| 5,150,006 A | 9/1992 | Van Slyke et al. |
| 5,151,629 A | 9/1992 | VanSlyke |

(Continued)

FOREIGN PATENT DOCUMENTS

| | | |
|---|---|---|
| EP | 0 732 868 | 9/1996 |
| EP | 0891121 | 1/1999 |

(Continued)

OTHER PUBLICATIONS

A. B. Tamayo, et al., "Synthesis and Characterization of Facial and Meridional Tris-cyclometalated Iridium(III) Complexes", Journal of the American Chemical Society, 2003, 125, pp. 7377-7387.

(Continued)

*Primary Examiner* — Marie R. Yamnitzky
(74) *Attorney, Agent, or Firm* — Global OLED Technology LLC

(57) ABSTRACT

An OLED device comprises a cathode, an anode, and located therebetween a light-emitting layer containing a host material and a tris-C^N-cyclometallated complex of Ir or Rh wherein at least one of the ligands comprises a substituted quinazoline moiety. The device provides useful emission and stability attributes.

10 Claims, 1 Drawing Sheet

(56) References Cited

U.S. PATENT DOCUMENTS

| | | | |
|---|---|---|---|
| 5,247,190 A | 9/1993 | Friend et al. | |
| 5,276,380 A | 1/1994 | Tang | |
| 5,283,182 A | 2/1994 | Powell et al. | |
| 5,294,870 A | 3/1994 | Tang et al. | |
| 5,405,709 A | 4/1995 | Littman et al. | |
| 5,484,922 A | 1/1996 | Moore et al. | |
| 5,503,910 A | 4/1996 | Matsuura et al. | |
| 5,552,678 A | 9/1996 | Tang et al. | |
| 5,593,788 A | 1/1997 | Shi et al. | |
| 5,608,287 A | 3/1997 | Hung et al. | |
| 5,645,948 A | 7/1997 | Shi et al. | |
| 5,677,572 A | 10/1997 | Hung et al. | |
| 5,683,823 A | 11/1997 | Shi et al. | |
| 5,688,551 A | 11/1997 | Littman et al. | |
| 5,703,436 A | 12/1997 | Forrest et al. | |
| 5,714,838 A | 2/1998 | Haight et al. | |
| 5,739,545 A | 4/1998 | Guha et al. | |
| 5,755,999 A | 5/1998 | Shi et al. | |
| 5,766,779 A | 6/1998 | Shi et al. | |
| 5,776,622 A | 7/1998 | Hung et al. | |
| 5,776,623 A | 7/1998 | Hung et al. | |
| 5,837,391 A | 11/1998 | Utsugi | |
| 5,851,709 A | 12/1998 | Grande et al. | |
| 5,928,802 A | 7/1999 | Shi et al. | |
| 5,935,720 A | 8/1999 | Chen et al. | |
| 5,935,721 A | 8/1999 | Shi et al. | |
| 5,969,474 A | 10/1999 | Arai | |
| 5,981,306 A | 11/1999 | Burrows et al. | |
| 6,013,384 A | 1/2000 | Kido et al. | |
| 6,020,078 A | 2/2000 | Chen et al. | |
| 6,066,357 A | 5/2000 | Tang et al. | |
| 6,097,147 A | 8/2000 | Baldo et al. | |
| 6,137,223 A | 10/2000 | Hung et al. | |
| 6,140,763 A | 10/2000 | Hung et al. | |
| 6,172,459 B1 | 1/2001 | Hung et al. | |
| 6,208,075 B1 | 3/2001 | Hung et al. | |
| 6,208,077 B1 | 3/2001 | Hung | |
| 6,226,890 B1 | 5/2001 | Boroson et al. | |
| 6,237,529 B1 | 5/2001 | Spahn | |
| 6,278,236 B1 | 8/2001 | Madathil et al. | |
| 6,284,393 B1 | 9/2001 | Hosokawa et al. | |
| 6,303,238 B1 | 10/2001 | Thompson et al. | |
| 6,337,492 B1 | 1/2002 | Jones et al. | |
| 6,413,656 B1 | 7/2002 | Thompson et al. | |
| 6,451,455 B1 | 9/2002 | Thompson et al. | |
| 6,458,475 B1 | 10/2002 | Adachi et al. | |
| 6,465,115 B2 | 10/2002 | Shi et al. | |
| 6,515,298 B2 | 2/2003 | Forrest et al. | |
| 6,573,651 B2 | 6/2003 | Adachi et al. | |
| 6,627,333 B2 | 9/2003 | Hatwar | |
| 6,835,835 B1 | 12/2004 | Huo | |
| 2001/0019782 A1* | 9/2001 | Igarashi et al. | 428/690 |
| 2002/0015859 A1 | 2/2002 | Watanabe et al. | |
| 2002/0025419 A1 | 2/2002 | Lee et al. | |
| 2002/0100906 A1 | 8/2002 | Takiguchi et al. | |
| 2002/0117662 A1 | 8/2002 | Nii | |
| 2002/0121638 A1 | 9/2002 | Grushin et al. | |
| 2002/0186214 A1 | 12/2002 | Siwinski | |
| 2002/0197511 A1 | 12/2002 | D'Andrade et al. | |
| 2003/0017361 A1 | 1/2003 | Thompson et al. | |
| 2003/0040627 A1 | 2/2003 | Fujii | |
| 2003/0054198 A1 | 3/2003 | Tsuboyama et al. | |
| 2003/0059646 A1 | 3/2003 | Kamatani et al. | |
| 2003/0068526 A1 | 4/2003 | Kamatani et al. | 428/690 |
| 2003/0068528 A1 | 4/2003 | Thompson et al. | |
| 2003/0068535 A1 | 4/2003 | Takiguchi et al. | |
| 2003/0072964 A1* | 4/2003 | Kwong et al. | 428/690 |
| 2003/0124381 A1 | 7/2003 | Thompson et al. | |
| 2003/0141809 A1 | 7/2003 | Furugori et al. | |
| 2003/0175553 A1 | 9/2003 | Thompson et al. | |
| 2004/0009367 A1 | 1/2004 | Hatwar | |
| 2004/0209115 A1 | 10/2004 | Thompson et al. | |
| 2004/0209116 A1 | 10/2004 | Ren et al. | |
| 2004/0255857 A1 | 12/2004 | Chow et al. | |
| 2005/0123795 A1 | 6/2005 | Lussier et al. | 428/690 |
| 2005/0191519 A1 | 9/2005 | Mishima et al. | 428/690 |
| 2005/0191527 A1 | 9/2005 | Fujii et al. | 428/690 |
| 2006/0134462 A1* | 6/2006 | Yeh et al. | 428/690 |

FOREIGN PATENT DOCUMENTS

| | | |
|---|---|---|
| EP | 1 009 041 | 6/2000 |
| EP | 1029909 | 8/2000 |
| EP | 1 076 368 | 2/2001 |
| EP | 1 182 244 | 2/2002 |
| EP | 1 187 235 | 3/2002 |
| EP | 1 238 981 | 9/2002 |
| EP | 1 239 526 | 9/2002 |
| EP | 1 244 155 | 9/2002 |
| EP | 1 469 533 | 10/2004 |
| EP | 1 478 032 | 11/2004 |
| EP | 1 480 280 | 11/2004 |
| JP | 3-234963 | 10/1991 |
| JP | 2001-267080 | 9/2001 |
| JP | 2003-59667 | 2/2003 |
| JP | 2003-73387 | 3/2003 |
| JP | 2003-73388 | 3/2003 |
| JP | 2003-73665 | 3/2003 |
| JP | 2004-200162 | 7/2004 |
| JP | 2004-311184 | 11/2004 |
| WO | WO 98/55561 | 12/1998 |
| WO | WO 00/18851 | 4/2000 |
| WO | WO 00/57676 | 9/2000 |
| WO | WO 00/70655 | 11/2000 |
| WO | WO 01/39234 | 5/2001 |
| WO | WO 01/41512 | 6/2001 |
| WO | WO 01/93642 | 12/2001 |
| WO | WO 02/15645 | 2/2002 |
| WO | WO 02/43449 | 5/2002 |
| WO | WO 02/074015 | 9/2002 |
| WO | WO 02071813 | 9/2002 |
| WO | WO 2004/018587 | 3/2004 |

OTHER PUBLICATIONS

Y. Song, et al., "Bright and Efficient, Non-Doped, Phosphorescent Organic Red-Light-Emitting Diodes", Adv. Funct. Mater., 14, Dec. 12, 2004, pp. 1221-1226.
Tang et al. [j. Applied Physics, vol. 65, pp. 3610-3616, 1989].
Dresner, "Double Injection Electroluminescence in Anthracene", RCA Review, vol. 30, pp. 322-334, 1969.
J. Kido et al., Phys. Lett., 65, 2124-2126 (1994).
C. Adachi, R. Kwong, and S.R. Forrest, Organic Electronics, 2, 37-43 (2001).
K.A. King, P.J. Spellane, and R.J. Watts, J. Am. Chem. Soc., 107, 1431-1432 (1985).
M.G. Colombo, T.C. Brunold, T. Reidener, H.U. Gudel, M. Fortsch, and H.-B. Burgi, Inorg. Chem., 33, (4494) 545-550 (1994).
M.A. Baldo, S. Lamansky, P.E. Burrows, M.E. Thompson, S.R. Forrest, Appl. Phys. Lett., 75, 4-6 (1999).
Appl. Phys. Lett., 79, 2082-2084 (2001), Adachi et al.
Duan et al., Adv. Mater., 15, 224-228 (2003).
S. Seo et al., SID 05 Digest, 806 (2005).
Hwang et al., Inorg. Chem., 44, 1344-1353 (2005).
T. Tsutsui, M.-J. Yang, M. Yahiro, K. Nakamura, T. Watanabe, T. Tsuji, Y. Fukuda, T. Wakimoto, S. Miyaguchi, Jpn. J. Appl. Phys., 38, L1502-L1504 (1999).

* cited by examiner

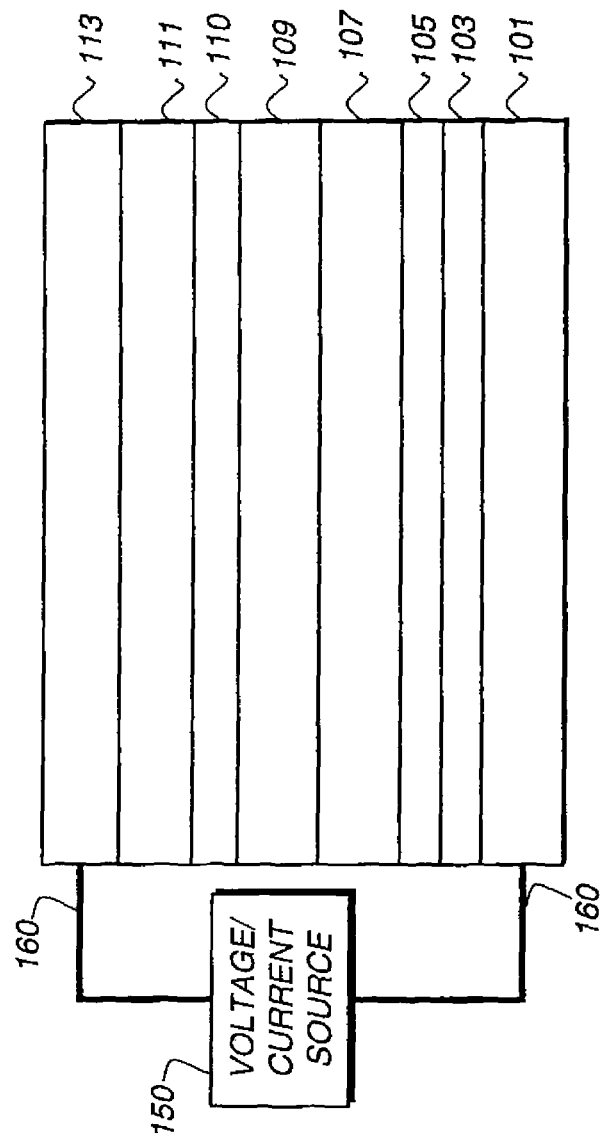

ELECTROLUMINESCENT DEVICE WITH QUINAZOLINE COMPLEX EMITTER

CROSS-REFERENCE TO RELATED APPLICATIONS

Reference is made to commonly assigned U.S. patent applications U.S. Ser. No. 10/945,337 filed Sep. 20, 2004 (now abandoned); U.S. Ser. No. 11/016,134 filed Dec. 17, 2004 (now U.S. Pat. No. 7,579,090); U.S. Ser. No. 10/945,338 filed Sep. 20, 2004 (now abandoned); U.S. Ser. No. 11/015,929 filed Dec. 17, 2004 (now U.S. Pat. No. 7,767,316), and U.S. Ser. No. 11/214,176, filed Aug. 29, 2005 (published as US 2007/0048544).

FIELD OF THE INVENTION

This invention relates to an organic light emitting diode (OLED) electroluminescent (EL) device comprising a light-emitting layer containing a host material and a phosphorescent light-emitting material that can provide desirable electroluminescent properties.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322-334, 1969; and Dresner U.S. Pat. No. 3,710,167, issued Jan. 9, 1973. The organic layers in these devices, usually composed of a polycyclic aromatic hydrocarbon, were very thick (much greater than 1 μm). Consequently, operating voltages were very high, often >100V.

More recent organic EL devices include an organic EL element consisting of extremely thin layers (e.g. <1.0 μm) between the anode and the cathode. Herein, the term "organic EL element" encompasses the layers between the anode and cathode electrodes. Reducing the thickness lowered the resistance of the organic layer and has enabled devices that operate much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al [*J. Applied Physics*, Vol. 65, Pages 3610-3616, 1989]. The light-emitting layer commonly consists of a host material doped with a guest material. Still further, there has been proposed in U.S. Pat. No. 4,769,292 a four-layer EL element comprising a hole-injecting layer (HIL), a hole-transporting layer (HTL), a light-emitting layer (LEL) and an electron transport/injection layer (ETL). These structures have resulted in improved device efficiency.

Many emitting materials that have been described as useful in an OLED device emit light from their excited singlet state by fluorescence. The excited singlet state is created when excitons formed in an OLED device transfer their energy to the excited state of the dopant. However, it is generally believed that only 25% of the excitons created in an EL device are singlet excitons. The remaining excitons are triplet, which cannot readily transfer their energy to the singlet-excited state of a dopant. This results in a large loss in efficiency since 75% of the excitons are not used in the light emission process.

Triplet excitons can transfer their energy to a dopant if it has a triplet excited state that is low enough in energy. If the triplet state of the dopant is emissive, it can produce light by phosphorescence. In many cases, singlet excitons can also transfer their energy to lowest singlet excited state of the same dopant. The singlet excited state can often relax, by an intersystem crossing process, to the emissive triplet excited state. Thus, it is possible, by the proper choice of host and dopant, to collect energy from both the singlet and triplet excitons created in an OLED device and to produce a very efficient phosphorescent emission.

Singlet and triplet states, and fluorescence, phosphorescence, and intersystem crossing are discussed in J. G. Calvert and J. N. Pitts, Jr., *Photochemistry* (Wiley, New York, 1966). Emission from triplet states is generally very weak for most organic compounds because the transition from triplet-excited state to singlet ground state is spin-forbidden. However, it is possible for compounds with states possessing a strong spin-orbit coupling interaction to emit strongly from triplet-excited states to the singlet ground state (phosphorescence). One such strongly phosphorescent compound is fac-tris(2-phenyl-pyridinato-N^C-)Iridium(III) (Ir(ppy)$_3$) that emits green light (K. A. King, P. J. Spellane, and R. J. Watts, *J. Am. Chem. Soc.*, 107, 1431 (1985), M. G. Colombo, T. C. Brunold, T. Reidener, H. U. Güdel, M. Fortsch, and H.-B. Bürgi, *Inorg. Chem.*, 33, 545 (1994)). Organic electroluminescent devices having high efficiency have been demonstrated with Ir(ppy)$_3$ as the phosphorescent material and 4,4'-N,N'-dicarbazole-biphenyl (CBP) as the host (M. A. Baldo, S. Lamansky, P. E. Burrows, M. E. Thompson, S. R. Forrest, *Appl. Phys. Lett.*, 75, 4 (1999), T. Tsutsui, M.-J. Yang, M. Yahiro, K. Nakamura, T. Watanabe, T. Tsuji, Y. Fukuda, T. Wakimoto, S. Miyaguchi, *Jpn. J. Appl. Phys.*, 38, L1502 (1999)). Additional disclosures of phosphorescent materials and organic electroluminescent devices employing these materials are found in U.S. Pat. No. 6,303,238 B1, WO 00/57676, WO 00/70655 and WO 01/41512 A1.

There is a continuing need to develop new phosphorescent materials for improved stability and to provide a wide range of hues. S. Seo and co-workers, *SID 05 Digest*, 806 (2005), Y. Chi et al., *Inorg. Chem.*, 44, 1344 (2005), C. Chen et al., *Adv. Funct. Mater.*, 14, 1221 (2004), and C. Cheng et al., *Adv. Mater.*, 15, 224 (2003) describe iridium complexes that include two C^N-cyclometallated quinazoline ligands and one ancillary ligand. The ancillary ligand is an anionic bidentate ligand that does not provide a carbon bonded to Ir. Although these materials are reported to have interesting properties it is generally the case that bis-cyclometallated metal complexes, although easier to synthesize, are less stable relative to tris-C^N-cyclometallated metal complexes.

Fujii et al, U.S. 2005/0191527 describes organometallic compounds with quinoxaline ligands including tris-C^N-cyclometallated complexes of iridium. Mishima et al., U.S. 2005/0191519 describes triplet emitters with various heterocyclic ligands. Some of these complexes are also tris-C^N-cyclometallated complexes of iridium, although none of the tris-C^N-cyclometallated complexes include a quinazoline ligand. However, many of the materials described in these disclosures emit at wavelengths that are too deep to be useful in a practical OLED device.

The nature of the host material is also critical to get good performance from the phosphorescent emitter. For example, U.S. Ser. No. 10/945,337 and U.S. Ser. No. 10/945,338 filed Sep. 20, 2004 (both now abandoned), and U.S. Ser. No. 11/015,929 and U.S. Ser. No. 11/016,134 filed Dec. 17, 2004 (now U.S. Pat. No. 7,767,316 and U.S. Pat. No. 7,579,090, respectively) describe an EL device in which the light emitting layer includes a hole-transporting compound, certain aluminum chelate materials, and a light-emitting phosphorescent compound. U.S. Ser. No. 11/214,176 filed Aug. 29, 2005 (published as US 2007/0048544), describes an EL device in which the light emitting layer includes a hole-transporting compound, certain gallium chelate materials, and a light-emitting phosphorescent compound.

Notwithstanding these developments, there remains a need for new phosphorescent materials to provide useful emission and stability attributes

SUMMARY OF THE INVENTION

The invention provides an OLED device that comprises a cathode, an anode, and located therebetween a light-emitting layer containing a host material and a tris-C^N-cyclometallated complex of Ir or Rh wherein at least one of the ligands comprises a substituted quinazoline moiety. The device provides useful emission and stability attributes.

BRIEF DESCRIPTION OF THE DRAWINGS

The FIGURE shows a schematic cross-sectional view of one embodiment of the device of the present invention.

DETAILED DESCRIPTION OF THE INVENTION

The organic light-emitting device (OLED) of the invention contains a cathode, a light-emitting layer, and an anode as described above. The light-emitting layer includes a host material and a tris C^N-cyclometallated complex of Ir or Rh wherein at least one of the ligands comprises a substituted quinazoline moiety. A quinazoline nucleus and its ring-numbering is shown below.

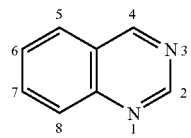

Desirably the metal forms a nitrogen-metal bond with one nitrogen of the quinazoline nucleus and forms a carbon-metal bond with a substituent on the quinazoline nucleus. Suitably, the substituent is at the 2 or the 4 position and includes at least one carbon-carbon double bond and the metal is bonded to one carbon of the double bond. Desirably the substituent is an aromatic group, such as a phenyl group, naphthyl group, or thienyl group.

The metal is Ir or Rh. Desirably the metal is Ir. In one embodiment the complex includes three independently selected substituted quinazoline moieties, and the metal is bonded to each of these moieties as described above.

In another embodiment, the substituted quinazoline moiety is a 2-phenylquinazoline group or a 4-phenylquinazoline group. In a similar embodiment, the complex includes three independently selected 2-phenylquinazoline groups or 4-phenylquinazoline groups.

The tris-C^N-cyclometallated complex may be a facial or a meridional isomer. Desirably the complex is a facial isomer, since they are often found to have higher emission quantum yield than the meridional isomer.

In another aspect of the invention, the tris C^N-cyclometallated complex is represented by Formula (1a) or Formula (1b).

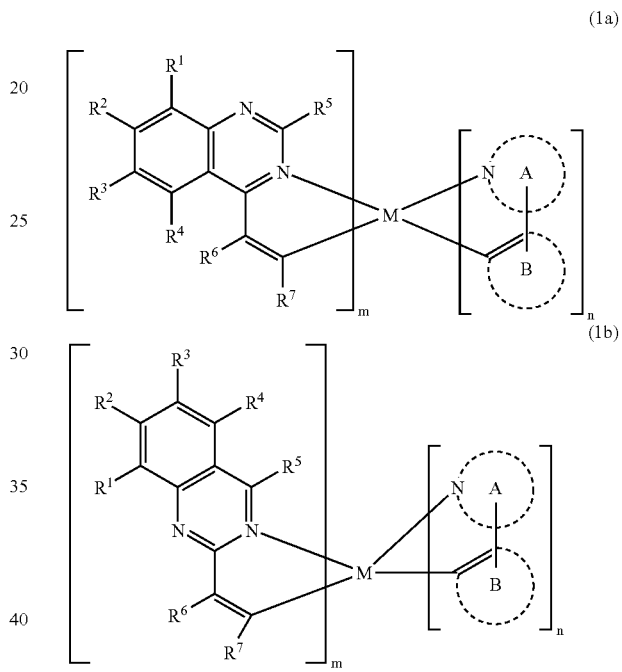

In Formulae (1a) and (1b), M represents Ir or Rh. Each $R^1$-$R^7$ represents hydrogen or an independently selected substituent group such as a phenyl group, a methyl group, or a trifluoromethyl group. Two of $R^1$-$R^7$ may combine to form a ring group, such as a fused benzene ring group. In one desirable embodiment $R^6$ and $R^7$ combine to form an aromatic group, such as a benzene group or thiophene group. In another embodiment, two of $R^1$-$R^5$ do not combine to form a fused ring, and thus the quinazoline nucleus does not have additional fused rings.

In Formulae (1a) and (1b), A represents a substituted or unsubstituted heterocyclic ring group containing at least one nitrogen atom, such as a pyridine ring group, a pyrazole ring group, an isoquinoline ring group, or a quinoline ring group. In the Formulae, B represents a substituted or unsubstituted aromatic or heteroaromatic ring. Examples of B include a phenyl ring group, a 4,6-difluorophenyl ring group, and a thienyl ring group. In one suitable embodiment, B represents an aryl group.

In the Formulae, m is an integer from 1 to 3; and n in an integer from 0 to 2 such that m+n=3. In one desirable embodiment, m is 3 and n is 0.

In a further aspect of the invention, the metal complex is represented by Formula (2a) or Formula (2b).

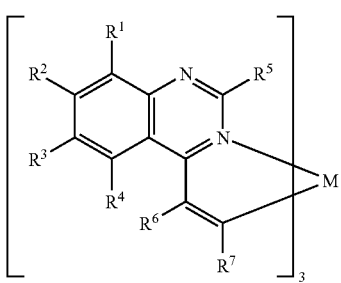

(2a)

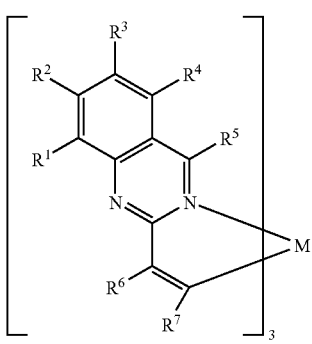

(2b)

In Formulae (2a) and (2b), M and $R^1$-$R^7$ have been described previously. In one desirable embodiment, $R^6$ and $R^7$, combine to form an aromatic ring.

In a another aspect of the invention, the metal complex is represented by (2c) or (2d):

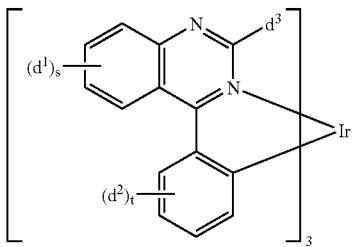

(2c)

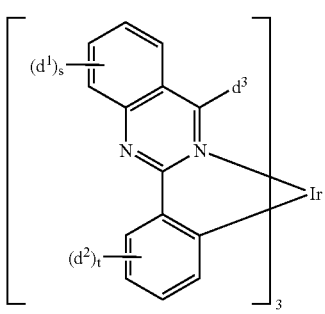

(2d)

In Formula (2c) and (2d), each $d^1$ and each $d^2$ represent independently selected substituents, such as a phenyl group or methyl group. Preferably adjacent substituents do not combine to form a fused ring.

In Formula (2c) and (2d), s is 0-4 and t is 0-4 and $d^3$ represents hydrogen or a substituent.

Tris-C^N-cyclometallated complexes of iridium and rhodium may be synthesized by methods described in the literature. However, it is often found that many of the methods are not generally applicable and work for only limited types of C^N-cyclometallating ligands. Through diligent experimentation in the synthetic methodology for tris-C^N-cyclometallating iridium complexes, the inventors have now found that the method recently disclosed in U.S. Ser. No. 10/879,657, filed Jun. 29, 2004, now allowed U.S. Pat. No. 7,005,522, results in efficient synthesis of the tris-C^N-cyclometallated complexes of the present invention having ligands that N-coordinate through quinazoline moieties. For cases of tris-C^N-cyclometallated complexes where the three C^N-cyclometallating ligands are not all the same, the methods described in U.S. Pat. No. 6,835,835, U.S. Ser. No. 11/015,910 (U.S. Pat. No. 7,417,146), Ser. No. 11/134,120 (U.S. Pat. No. 7,476,739), and U.S. Ser. No. 11/240,288 filed Sep. 30, 2005, (U.S. Pat. No. 7,517,984) may be used.

Illustrative examples of Formula (1) and Formula (2) compounds are listed below.

Inv-1

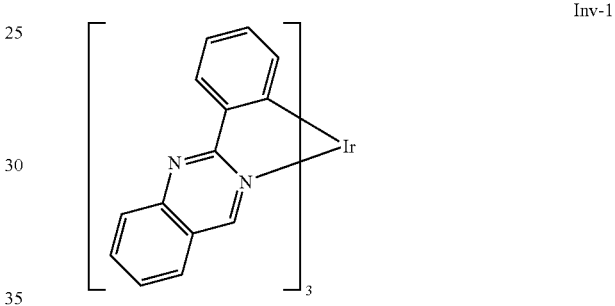

Inv-2

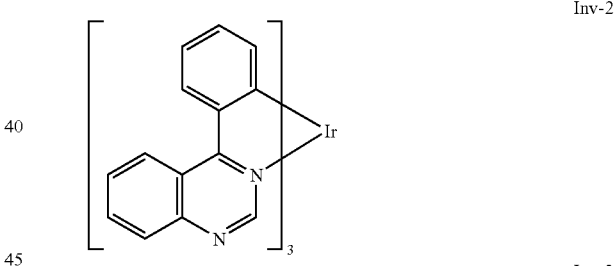

Inv-3

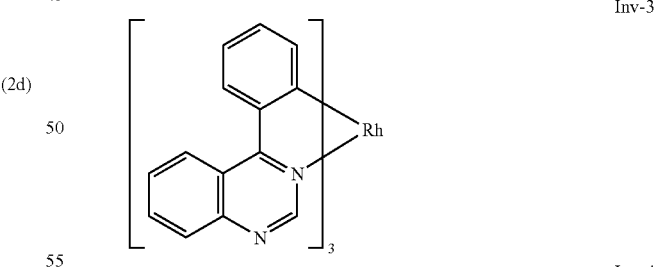

Inv-4

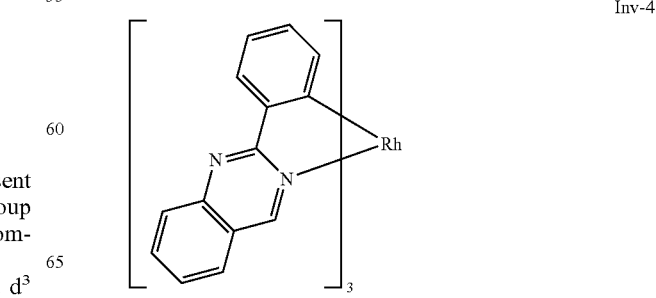

Inv-5
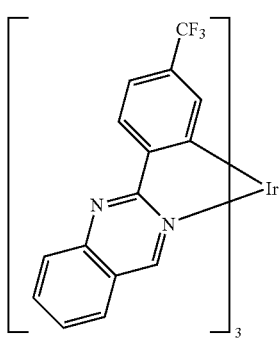
Inv-6
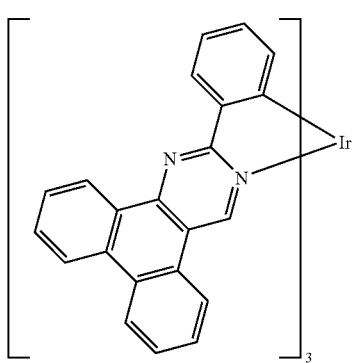
Inv-7
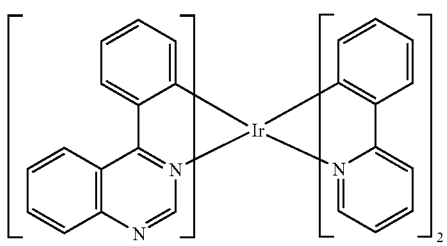
Inv-8
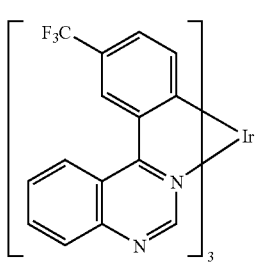
Inv-9
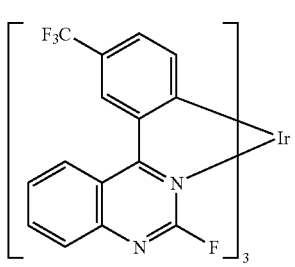
Inv-10
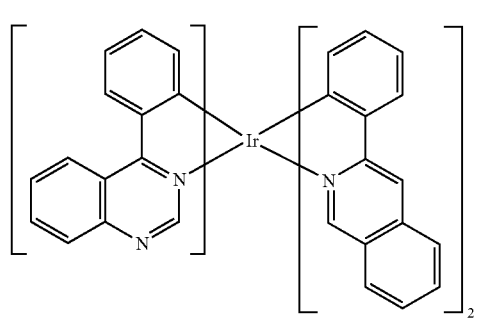
Inv-11
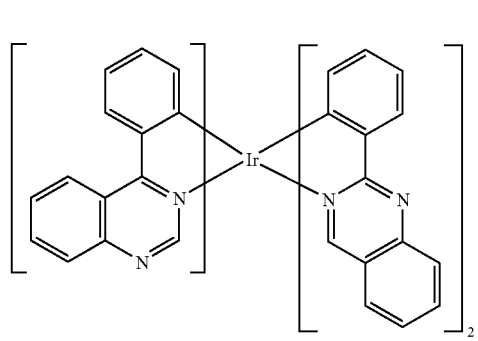
Inv-12
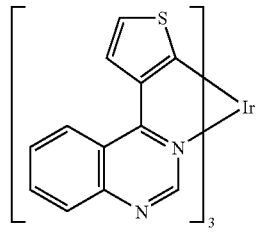
Inv-13
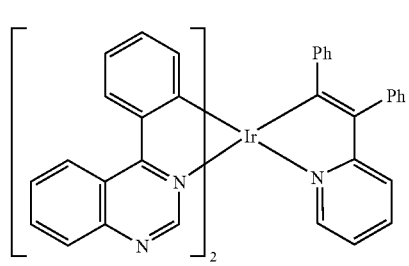
Inv-14
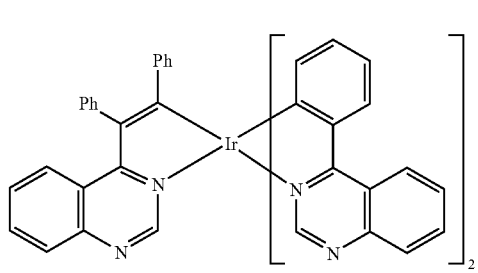

Inv-15 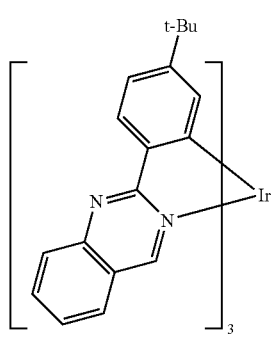
Inv-16 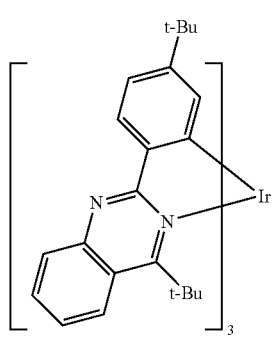
Inv-17 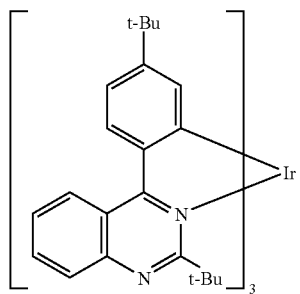
Inv-18 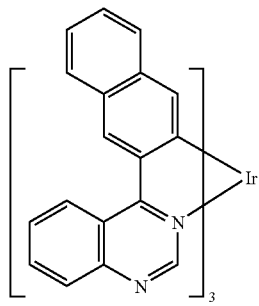
Inv-19 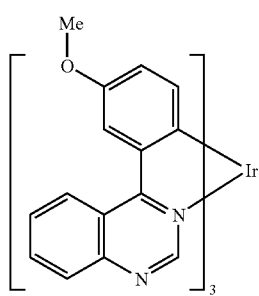
Inv-20 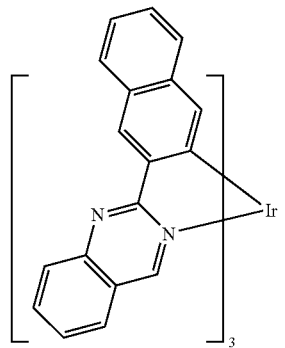
Inv-21 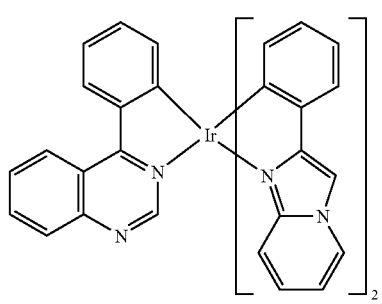
Inv-22 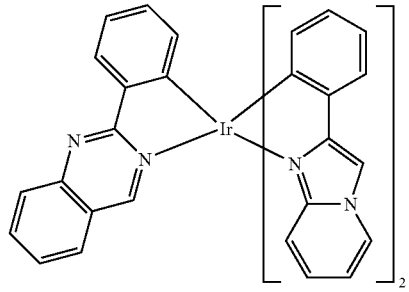
Inv-23 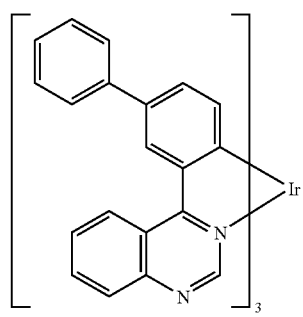
Inv-24 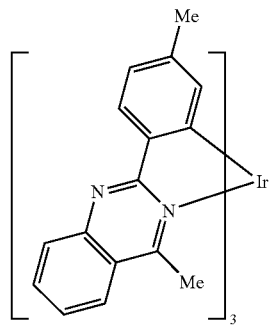

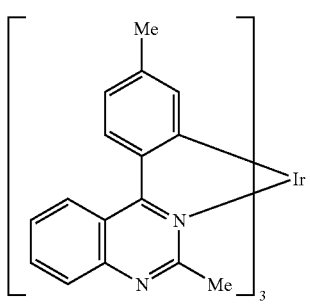

Inv-25

The light-emitting layer also includes at least one host material. Desirably the host material has a triplet energy higher than or equal to the triplet energy of the metal complex. Triplet energy is conveniently measured by any of several means, as discussed for instance in S. L. Murov, I. Carmichael, and G. L. Hug, *Handbook of Photochemistry*, 2nd ed. (Marcel Dekker, New York, 1993).

In the absence of experimental data the triplet energies may be estimated in the following manner. The triplet state energy for a molecule is defined as the difference between the ground state energy (E(gs)) of the molecule and the energy of the lowest triplet state (E(ts)) of the molecule, both given in eV. These energies can be calculated using the B3LYP method as implemented in the Gaussian98 (Gaussian, Inc., Pittsburgh, Pa.) computer program. The basis set for use with the B3LYP method is defined as follows: MIDI! for all atoms for which MIDI! is defined, 6-31G* for all atoms defined in 6-31G* but not in MIDI!, and either the LACV3P or the LANL2DZ basis set and pseudopotential for atoms not defined in MIDI! or 6-31G*, with LACV3P being the preferred method. For any remaining atoms, any published basis set and pseudopotential may be used. MIDI!, 6-31G* and LANL2DZ are used as implemented in the Gaussian98 computer code and LACV3P is used as implemented in the Jaguar 4.1 (Schrodinger, Inc., Portland Oreg.) computer code. The energy of each state is computed at the minimum-energy geometry for that state. The difference in energy between the two states is further modified by Equation 1 to give the triplet state energy (E(t)):

$$E(t)=0.84*(E(ts)-E(gs))+0.35 \quad (1)$$

For polymeric or oligomeric materials, it is sufficient to compute the triplet energy over a monomer or oligomer of sufficient size so that additional units do not substantially change the computed triplet energy of the material.

Suitable host materials should be selected so that the triplet exciton can be transferred efficiently from the host material to the phosphorescent material. For this transfer to occur, it is a highly desirable condition that the excited state energy of the phosphorescent material be lower than the difference in energy between the lowest triplet state and the ground state of the host, although efficient emission has been reported for devices where the host has a lower triplet energy than the dopant by M. A. Baldo, M. E. Thompson, S. K. Forrest and co-workers, *Appl. Phys. Lett.*, 79, 2082 (2001). However, the band gap of the host should not be chosen so large as to cause an unacceptable increase in the drive voltage of the OLED. Suitable host materials are described in WO 00/70655; WO 01/39234; WO 01/93642; WO 02/074015; WO 02/15645, and U.S. 20020117662. Suitable hosts include certain aryl amines, triazoles, indoles and carbazole compounds. Examples of desirable hosts are 4,4'-N,N'-dicarbazole-biphenyl (CBP), 2,2'-dimethyl-4,4'-N,N'-dicarbazole-biphenyl, m-(N,N'-dicarbazole)benzene, and poly(N-vinylcarbazole), including their derivatives. In one embodiment, the host material includes a carbazole derivative.

Types of triplet host materials may be categorized according to their charge transport properties. The two major types are those that are predominantly electron transporting and those that are predominantly hole transporting. It should be noted that some host materials, which may be categorized as transporting dominantly one type of charge, may transport both types of charges, especially in certain device structures, for example CBP which is described in C. Adachi, R. Kwong, and S. R. Forrest, *Organic Electronics*, 2, 37-43 (2001). Another type of host are those having a wide energy gap between the HOMO and LUMO such that they do not readily transport charges of either type and instead rely on charge injection directly into the phosphorescent dopant molecules.

A desirable electron transporting host may be any suitable electron transporting compound, such as benzazole, phenanthroline, 1,3,4-oxadiazole, triazole, triazine, or triarylborane, as long as it has a triplet energy that is higher than that of the phosphorescent emitter to be employed.

A preferred class of benzazoles is described by Jianmin Shi et al. in U.S. Pat. No. 5,645,948 and U.S. Pat. No. 5,766,779. Such compounds are represented by structural formula (PHF-1):

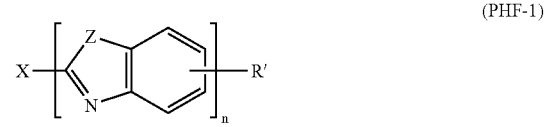

(PHF-1)

In formula (PHF-1), n is selected from 2 to 8;
Z is independently O, NR or S;
R and R' are individually hydrogen; alkyl of from 1 to 24 carbon atoms, for example, propyl, t-butyl, heptyl, and the like; aryl or hetero-atom substituted aryl of from 5 to 20 carbon atoms, for example, phenyl and naphthyl, furyl, thienyl, pyridyl, quinolinyl and other heterocyclic systems; or halo such as chloro, fluoro; or atoms necessary to complete a fused aromatic ring; and X is a linkage unit consisting of carbon, alkyl, aryl, substituted alkyl, or substituted aryl, which conjugately or unconjugately connects the multiple benzazoles together.

An example of a useful benzazole is 2,2',2"-(1,3,5-phenylene)tris[1-phenyl-1H-benzimidazole] (TPBI) represented by a formula (PHF-2) shown below:

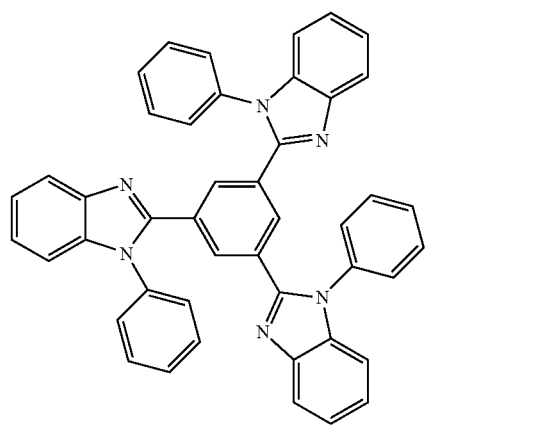

(PHF-2)

Another class of the electron transporting materials suitable for use as a host includes various substituted phenanthrolines as represented by formula (PHF-3):

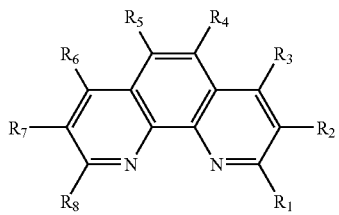
(PHF-3)

In formula (PHF-3), $R_1$-$R_8$ are independently hydrogen, alkyl group, aryl or substituted aryl group, and at least one of $R_1$-$R_8$ is aryl group or substituted aryl group.

Examples of suitable materials are 2,9-dimethyl-4,7-diphenyl-phenanthroline (BCP) (see formula (PH-1)) and 4,7-diphenyl-1,10-phenanthroline (Bphen) (see formula (PH-2)).

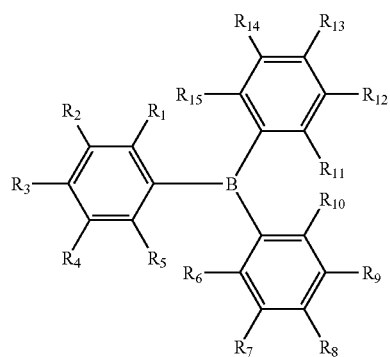
(PHF-5)

wherein $R_1$-$R_{15}$ are independently hydrogen, fluoro, cyano, trifluoromethyl, sulfonyl, alkyl, aryl or substituted aryl group.

Specific representative embodiments of the triarylboranes include:

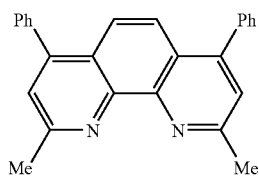
(PH-1)

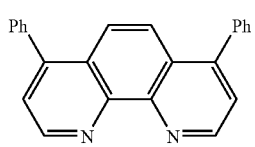
(PH-2)

A triarylborane that functions as an electron transporting host may be selected from compounds having the chemical formula (PHF-4):

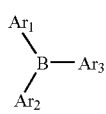
(PHF-4)

wherein $Ar_1$ to $Ar_3$ are independently an aromatic hydrocarbocyclic group or an aromatic heterocyclic group, which may have one or more substituent. It is preferable that compounds having the above structure are selected from formula (PHF-5):

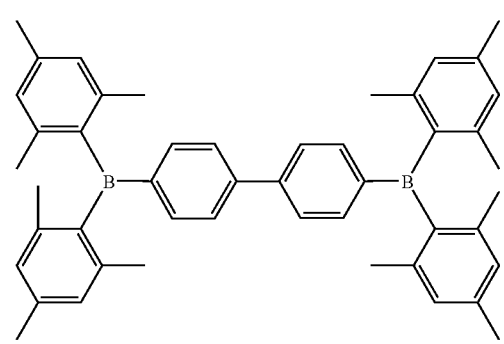
(PH-3)

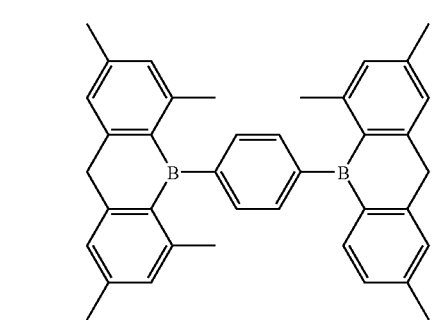
(PH-4)

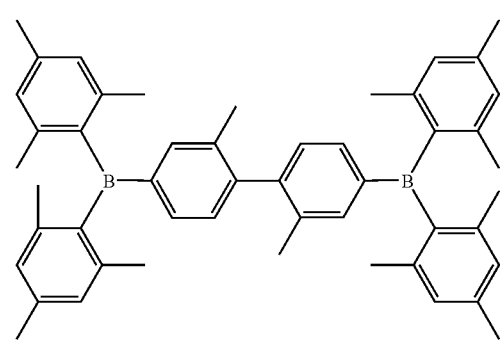
(PH-5)

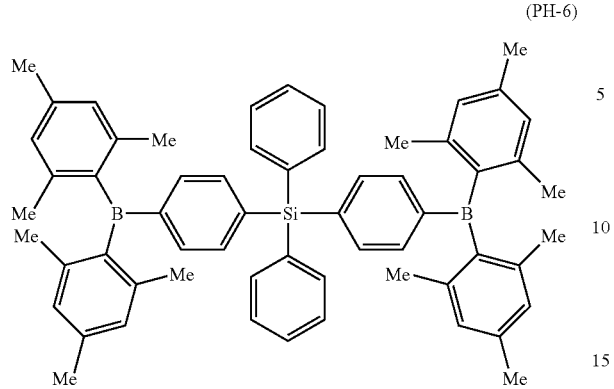

(PH-6)

An electron-transporting host may be selected from substituted 1,3,4-oxadiazoles. Illustrative of the useful substituted oxadiazoles are the following:

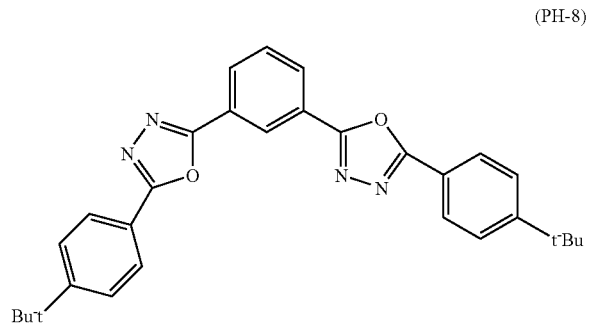

(PH-8)

An electron-transporting host may be selected from substituted 1,2,4-triazoles. An example of a useful triazole is 3-phenyl-4-(1-naphthyl)-5-phenyl-1,2,4-triazole represented by formula (PHF-6):

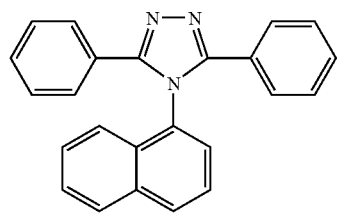

(PHF-6)

The electron transporting host may be selected from substituted 1,3,5-triazines. Examples of suitable materials are:
2,4,6-tris(diphenylamino)-1,3,5-triazine;
2,4,6-tricarbazolo-1,3,5-triazine;
2,4,6-tris(N-phenyl-2-naphthylamino)-1,3,5-triazine;
2,4,6-tris(N-phenyl-1-naphthylamino)-1,3,5-triazine;
4,4',6,6'-tetraphenyl-2,2'-bi-1,3,5-triazine;
2,4,6-tris([1,1':3',1''-terphenyl]-5'-yl)-1,3,5-triazine.

In one embodiment, the host material includes a material that is an aluminum or gallium complex. Particularly useful hosts materials are represented by Formula (PHF-7) also referred to herein as Formula (3).

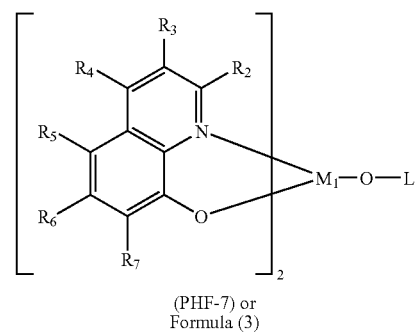

(PHF-7) or Formula (3)

In Formula (3), $M_1$ represents Al or Ga. $R_2$-$R_7$ represent hydrogen or an independently selected substituent. Desirably, $R_2$ represents an electron-donating group, such as a methyl group. Suitably, $R_3$ and $R_4$ each independently represent hydrogen or an electron donating substituent. Preferably, $R_5$, $R_6$, and $R_7$ each independently represent hydrogen or an electron-accepting group. Adjacent substituents, $R_2$-$R_7$, may combine to form a ring group. L is an aromatic moiety linked to the aluminum by oxygen, which may be substituted with substituent groups such that L has from 6 to 30 carbon atoms. Illustrative examples of Formula (3) materials are listed below.

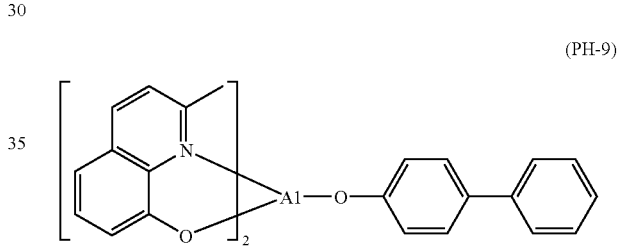

(PH-9)

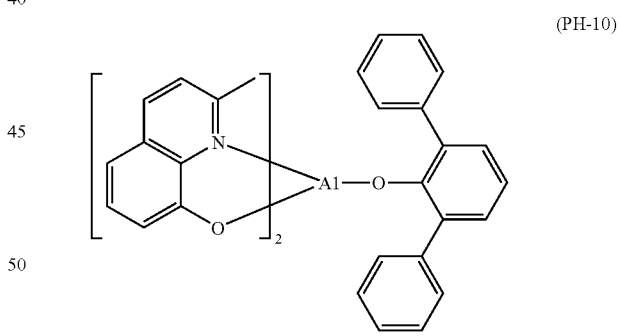

(PH-10)

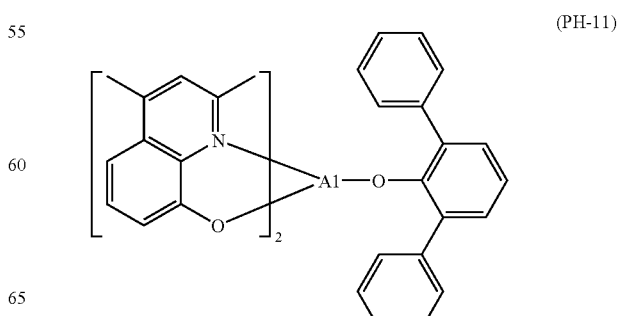

(PH-11)

-continued

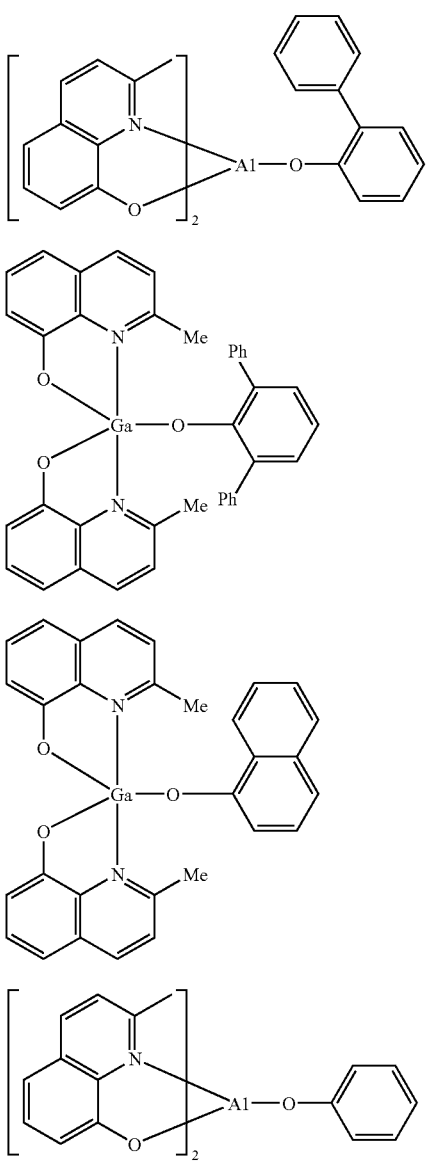

(PH-12)

(PH-13)

(PH-14)

(PH-15)

A suitable class of hole transporting compounds for use as a host are aromatic tertiary amines, by which it is understood to be compounds containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. in U.S. Pat. No. 3,180,730. Other suitable triarylamines substituted with one or more vinyl radicals and/or comprising at least one active hydrogen containing group are disclosed by Brantley et al. in U.S. Pat. No. 3,567,450 and U.S. Pat. No. 3,658,520.

A more preferred class of aromatic tertiary amines are those which include at least two aromatic tertiary amine moieties as described in U.S. Pat. No. 4,720,432 and U.S. Pat. No. 5,061,569. Such as the tetraaryldiamines. Desirable tetraaryldiamines include two diarylamino groups, such as indicated by formula (PHF-8):

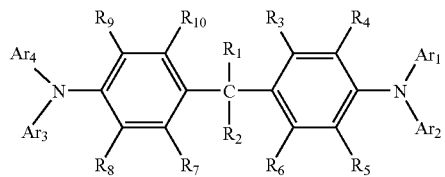

(PHF-8)

wherein each Are is an independently selected arylene group, such as a phenylene or anthracene moiety,
n is selected from 1 to 4, and
$R_1$-$R_4$ are independently selected aryl groups.

In a typical embodiment, at least one of $R_1$-$R_4$ is a polycyclic fused ring structure, e.g., a naphthalene. However, when the emission of the dopant is blue or green in color it is less preferred for the host material to have a polycyclic fused ring substituent.

Representative examples of the useful compounds include the following:
4,4'-Bis[N-(1-naphthyl)-N-phenylamino]biphenyl (NPB);
4,4'-Bis[N-(1-naphthyl)-N-(2-naphthyl)amino]biphenyl (TNB);
4,4'-Bis[N-(3-methylphenyl)-N-phenylamino]biphenyl (TPD);
4,4'-Bis-diphenylamino-terphenyl;
2,6,2',6'-tetramethyl-N,N,N',N'-tetraphenyl-benzidine.4,4',4''-tris[(3-methylphenyl)phenylamino]triphenylamine (MTDATA);
4,4',4''-tris(N,N-diphenyl-amino)triphenylamine (TDATA);
N,N-bis[2,5-dimethyl-4-[(3-methylphenyl)phenylamino] phenyl]-2,5-dimethyl-N'-(3-methylphenyl)-N'-phenyl-1, 4-benzenediamine.

In one desirable embodiment the hole-transporting host comprises a material of formula (PHF-9):

(PHF-9)

In formula (PHF-9), $R_1$ and $R_2$ represent substituents, provided that $R_1$ and $R_2$ can join to form a ring. For example, $R_1$ and $R_2$ can be methyl groups or join to form a cyclohexyl ring;
$Ar_1$-$Ar_4$ represent independently selected aromatic groups, for example phenyl groups or tolyl groups;
$R_3$-$R_{10}$ independently represent hydrogen, alkyl, substituted alkyl, aryl, substituted aryl group.

Examples of suitable materials include, but are not limited to:
1,1-Bis(4-(N,N-di-p-tolylamino)phenyl)cyclohexane (TAPC);
1,1-Bis(4-(N,N-di-p-tolylamino)phenyl)cyclopentane;
4,4'-(9H-fluoren-9-ylidene)bis[N,N-bis(4-methylphenyl)-benzenamine;
1,1-Bis(4-(N,N-di-p-tolylamino)phenyl)-4-phenylcyclohexane;
1,1-Bis(4-(N,N-di-p-tolylamino)phenyl)-4-methylcyclohexane;
1,1-Bis(4-(N,N-di-p-tolylamino)phenyl)-3-phenylpropane:
Bis[4-(N,N-diethylamino)-2-methylphenyl](4-methylpenyl) methane;
Bis[4-(N,N-diethylamino)-2-methylphenyl](4-methylphenyl)ethane;

4-(4-Diethylaminophenyl)triphenylmethane;
4,4'-Bis(4-diethylaminophenyl)diphenylmethane.

A useful class of compounds for use as the hole transporting host includes carbazole derivatives such as those represented by formula (PHF-10):

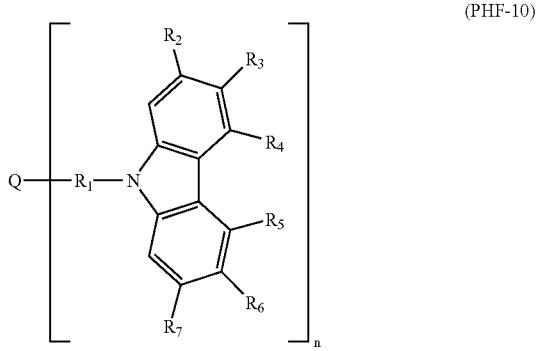

(PHF-10)

In formula (PHF-10), Q independently represents nitrogen, carbon, silicon, a substituted silicon group, an aryl group, or substituted aryl group, preferably a phenyl group;

$R_1$ is preferably an aryl or substituted aryl group, and more preferably a phenyl group, substituted phenyl, biphenyl, substituted biphenyl group;

$R_2$ through $R_7$ are independently hydrogen, alkyl, phenyl or substituted phenyl group, aryl amine, carbazole, or substituted carbazole;

and n is selected from 1 to 4.

Illustrative useful substituted carbazoles are the following:
4-(9H-carbazol-9-yl)-N,N-bis[4-(9H-carbazol-9-yl)phenyl]-benzenamine (TCTA);
4-(3-phenyl-9H-carbazol-9-yl)-N,N-bis[4(3-phenyl-9H-carbazol-9-yl)phenyl]-benzenamine;
9,9'-[5'-[4-(9H-carbazol-9-yl)phenyl][1,1':3',1"-terphenyl]-4,4"-diyl]bis-9H-carbazole.
3,5-bis(9-carbazolyl)tetraphenylsilane (SimCP).

In one suitable embodiment the hole-transporting host comprises a material of formula (PHF-11):

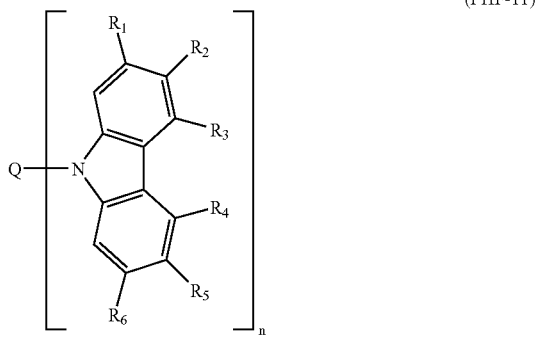

(PHF-11)

In formula (PHF-11), n is selected from 1 to 4;

Q independently represents phenyl group, substituted phenyl group, biphenyl, substituted biphenyl group, aryl, or substituted aryl group;

$R_1$ through $R_6$ are independently hydrogen, alkyl, phenyl or substituted phenyl, aryl amine, carbazole, or substituted carbazole.

Examples of suitable materials are the following:
9,9'-(2,2'-dimethyl[1,1'-biphenyl]-4,4'-diyl)bis-9H-carbazole (CDBP);
9,9'-[1,1'-biphenyl]-4,4'-diylbis-9H-carbazole (CBP);
9,9'-(1,3-phenylene)bis-9H-carbazole (mCP);
9,9'-(1,4-phenylene)bis-9H-carbazole;
9,9',9"-(1,3,5-benzenetriyl)tris-9H-carbazole;
9,9'-(1,4-phenylene)bis[N,N,N',N'-tetraphenyl-9H-carbazole-3,6-diamine;
9-[4-(9H-carbazol-9-yl)phenyl]-N,N-diphenyl-9H-carbazol-3-amine;
9,9'-(1,4-phenylene)bis[N,N-diphenyl-9H-carbazol-3-amine;
9-[4-(9H-carbazol-9-yl)phenyl]-N,N,N',N'-tetraphenyl-9H-carbazole-3,6-diamine.

Host materials that are electron-transporting or hole-transporting with some electron transporting properties, such as carbazoles, are generally more desirable when used as a single host material. This is especially true for typical phosphorescent dopants that are hole-trapping or capable of accepting injected holes. Less preferable are host materials that are primarily hole transporting and have little electron transporting properties, such as triarlyamines. Injecting electrons into these latter hole-transporting hosts may be difficult because of their relatively high LUMO energies.

Host materials may comprise a mixture of two or more host materials. Particularly useful is a mixture comprising at least one each of an electron-transporting and a hole-transporting co-host. The optimum concentration of the hole transporting co-host(s) may be determined by experimentation and may be within the range 5 to 60 volume % of the total of the hole- and electron transporting co-host materials in the light emitting layer, and is often found to be in the range 15 to 30 vol. %. It is further noted that electron-transporting molecules and hole-transporting molecules may be covalently joined together to form single host molecules having both electron-transporting and hole-transporting properties.

In one aspect of the invention, the host material of the light-emitting layer includes a host of Formula (3) and at least one additional host compound, also referred to as a co-host, is present. Desirably the co-host is a compound capable of transporting holes.

The co-host having hole-transporting properties may be any suitable hole-transporting compound, such as a triarylamine or carbazole, as long as it has a triplet energy that is higher than that of the phosphorescent dopant to be employed. The optimum concentration of the hole transporting co-host relative to the host of Formula (3) in the present invention may be determined by experimentation. The concentration of the hole transporting co-host is frequently within the range 5 to 60% of the light-emitting layer by volume, and is often found to be in the range 10 to 30%, or commonly in the range of 10 to 20%.

In one desirable embodiment, the co-host is represented by Formula (4).

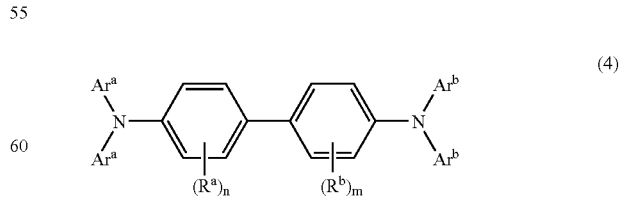

(4)

In Formula (4), each $Ar^a$ and each $Ar^b$ may be the same or different and each independently represents an aromatic group, such as a phenyl group or a naphthyl group. Each $R^a$ and each $R^b$ may be the same or different and each independently represents a substituent group; n and m independently are 0-4. In one suitable embodiment, n is 0 and m is 0.

A wide energy gap host material may be any suitable compound having a large HOMO-LUMO gap such that the HOMO and LUMO of the phosphorescent emissive material are within the HOMO and LUMO for the host. In this case, the phosphorescent emissive material acts as the primary charge carrier for both electrons and holes, as well as the site for the trapping of excitons. Often the phosphorescent dopants for use with the wide energy gap hosts are selected to have electron-withdrawing substituents to facilitate electron injection. The "wide energy gap" host material functions as a non-charge carrying material in the system. Such a combination may lead to high operation voltage of the device, as the concentration of the charge-carrying dopant is typically below 10% in the emissive layer.

Thompson et al. disclosed in U.S. 2004/0209115 and U.S. 2004/0209116 a group of wide energy gap hosts having triplet energies suitable for blue phosphorescent OLEDs. Such compounds include those represented by structural formula (PHF-12):

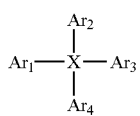

(PHF-12)

wherein:

X is Si or Pb; $Ar_1$, $Ar_2$, $Ar_3$ and $Ar_4$ are each an aromatic group independently selected from phenyl and high triplet energy heterocyclic groups such as pyridine, pyrazole, thiophene, etc. It is believed that the HOMO-LUMO gaps in these materials are large due to the electronically isolated aromatic units, and the lack of any conjugating substituents.

Illustrative examples of this type of hosts include:

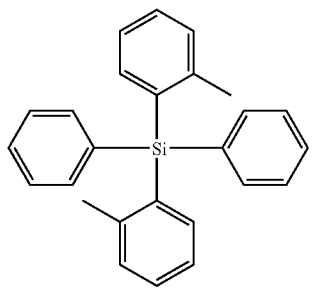

(PH-16)

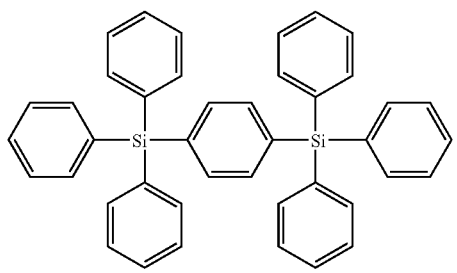

(PH-17)

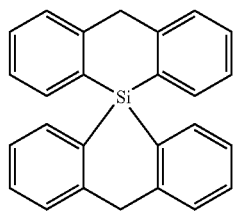

(PH-18)

In many known hosts and device architectures for phosphorescent OLEDs, the optimum concentration of the phosphorescent dopant for luminous efficiency is found to be about 1 to 20 vol % and often 6 to 8 vol % relative to the host material. In one aspect of the invention, wherein a mixture of an electron-transporting host and a hole-transporting co-host is present in the light-emitting layer, a phosphorescent material concentration from about 0.5% to about 6% often provides high luminous efficiencies.

In addition to suitable hosts, an EL device employing a phosphorescent material often is more efficient if there is at least one exciton- or hole-blocking layer on the cathode side of the emitting layer. Efficiency can also often be improved if there are one or more exciton- or electron-blocking layers on the anode side of the emitting layer. These additional layers help confine the excitons or electron-hole recombination centers to the light-emitting layer comprising the host and emitting material.

An exciton- or hole-blocking layer is desirably placed between the electron-transporting layer and the light-emitting layer, Layer 109 in the FIGURE. The ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in WO 00/70655A2 and WO 01/93642 A1. Two examples of useful materials are bathocuproine (BCP) and bis(2-methyl-8-quinolinolato)(4-phenylphenolato)Aluminum(III) (BAlq). Metal complexes other than BAlq are also known to block holes and excitons as described in U.S. 20030068528. Depending on the nature of the electron-transporting material and the configuration of the LEL, this blocking layer, in certain cases, can be entirely omitted.

In another embodiment, an exciton- or electron-blocking layer would be placed between the hole-transporting layer and the light-emitting layer (this layer is not shown in the FIGURE). As an example, U.S. 2003/0175553 describes the use of fac-tris(1-phenylpyrazolato-N,$C^{2'}$)iridium(III) (Ir (ppz)$_3$) in an electron/exciton blocking layer. U.S. Ser. No. 11/016,108 of Marina E. Kondakova et al., filed Dec. 17, 2004, now U.S. Pat. No. 7,597,967 describes further examples of exciton-blocking layers. Depending on the nature of the hole-transporting material and the configuration of the LEL, this blocking layer, in certain cases, can be entirely omitted.

Unless otherwise specifically stated, use of the term "substituted" or "substituent" means any group or atom other than hydrogen. Unless otherwise provided, when a group, compound or formula containing a substitutable hydrogen is referred to, it is also intended to encompass not only the substituent's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl) ureido, N,N-(2,5-di-t-pentylphenyl)-N'-ethylureido, and t-butylcarbonamido; sulfonamido, such as methyl sulfonamido, benzenesulfonamido, p-tolylsulfonamido, p-dodecyl-benzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur or phosphorous, such as pyridyl, thienyl, furyl, azolyl, thiazolyl, oxazolyl, imidazolyl, pyrazolyl, pyrazinyl, pyrimidinyl, pyrolidinonyl, quinolinyl, isoquinolinyl, 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

It is well within the skill of the art to determine whether a particular group is electron donating or electron accepting. The most common measure of electron donating and accepting properties is in terms of Hammett σ values. Hydrogen has a Hammett σ value of zero, while electron donating groups have negative Hammett σ values and electron accepting groups have positive Hammett σ values. Lange's handbook of Chemistry, $12^{th}$ Ed., McGraw Hill, 1979, Table 3-12, pp. 3-134 to 3-138, here incorporated by reference, lists Hammett σ values for a large number of commonly encountered groups. Hammett σ values are assigned based on phenyl ring substitution, but they provide a practical guide for qualitatively selecting electron donating and accepting groups.

Suitable electron donating groups may be selected from —R', —OR', and —NR'(R") where R' is a hydrocarbon containing up to 6 carbon atoms and R" is hydrogen or R'. Specific examples of electron donating groups include methyl, ethyl, phenyl, methoxy, ethoxy, phenoxy, —N(CH$_3$)$_2$, —N(CH$_2$CH$_3$)$_2$, —NHCH$_3$, —N(C$_6$H$_5$)$_2$, —N(CH$_3$)(C$_6$H$_5$), and —NHC$_6$H$_5$.

Suitable electron accepting groups may be selected from the group consisting of cyano, α-haloalkyl, α-haloalkoxy, amido, sulfonyl, carbonyl, carbonyloxy and oxycarbonyl substituents containing up to 10 carbon atoms. Specific examples include —CN, —F, —CF$_3$, —OCF$_3$, —CONHC$_6$H$_5$, —SO$_2$C$_6$H$_5$, —COC$_6$H$_5$, —CO$_2$C$_6$H$_5$, and —OCOC$_6$H$_5$.

For the purpose of this invention, also included in the definition of a heterocyclic ring are those rings that include coordinate or dative bonds. The definition of a coordinate bond can be found in Grant & Hackh's Chemical Dictionary, page 91. In essence, a coordinate bond is formed when electron rich atoms such as O or N, donate a pair of electrons to electron deficient atoms such as Al or B.

General Device Architecture

The present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers wherein the present invention can be successfully practiced. The essential requirements of an OLED are an anode, a cathode, and an organic light-emitting layer located between the anode and cathode. Additional layers may be employed as more fully described hereafter.

A typical structure, especially useful for of a small molecule device, is shown in the FIGURE and is comprised of a substrate 101, an anode 103, a hole-injecting layer 105, a hole-transporting layer 107, a light-emitting layer 109, a hole- or exciton-blocking layer 110, an electron-transporting layer 111, and a cathode 113. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

The anode and cathode of the OLED are connected to a voltage/current source 150 through electrical conductors 160. The OLED is operated by applying a potential between the anode and cathode such that the anode is at a more positive potential than the cathode. Holes are injected into the organic EL element from the anode and electrons are injected into the organic EL element at the cathode. Enhanced device stability can sometimes be achieved when the OLED is operated in an AC mode where, for some time period in the cycle, the potential bias is reversed and no current flows. An example of an AC driven OLED is described in U.S. Pat. No. 5,552,678.

Substrate

The OLED device of this invention is typically provided over a supporting substrate 101 where either the cathode or anode can be in contact with the substrate. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials. The electrode in contact with the substrate is conveniently referred to as the bottom electrode. Conventionally, the bottom electrode is the anode, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. For applications where the EL emission is viewed through the top electrode, the transmissive characteristic of the bottom support can be light transmissive, light absorbing or light reflective. Substrates for use in this case include, but are not limited to, glass, plastic, semiconductor materials, silicon, ceramics, and circuit board materials. It is necessary to provide in these device configurations a light-transparent top electrode.

Anode

When the desired electroluminescent light emission (EL) is viewed through the anode, the anode 103 should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Hole-Injecting Layer (HIL)

A hole-injecting layer 105 may be provided between the anode and the hole-transporting layer. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,127,004, U.S. Pat. No. 6,208,075 and U.S. Pat. No. 6,208,077, some aromatic amines, for example, MTDATA (4,4',4"-tris[(3-methylphenyl)phenylamino]triphenylamine), and inorganic oxides including vanadium oxide (VOx), molybdenum oxide (MoOx), and nickel oxide (NiOx). Alternative hole-injecting materials reportedly useful in organic EL devices are described in EP 0 891 121 A1 and EP 1 029 909 A1.

The thickness of a hole injection layer containing a plasma-deposited fluorocarbon polymer can be in the range of 0.2 nm to 15 nm and suitably in the range of 0.3 to 1.5 nm.

Hole-Transporting Layer (HTL)

It is usually advantageous to have a hole transporting layer 107 deposited between the anode and the emissive layer. A hole transporting material deposited in said hole transporting layer between the anode and the light emitting layer may be the same or different from a hole transporting compound used as a co-host or in exciton blocking layer according to the invention. The hole transporting layer may optionally include a hole injection layer. The hole transporting layer may include more than one hole transporting compound, deposited as a blend or divided into separate layers.

The hole-transporting layer contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. Nos. 3,567,450 and 3,658,520.

A more preferred class of aromatic tertiary amines is those which include at least two aromatic tertiary amine moieties as described in U.S. Pat. No. 4,720,432 and U.S. Pat. No. 5,061,569. Such compounds include those represented by structural formula (HT1):

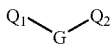
(HT1)

Wherein:

$Q_1$ and $Q_2$ are independently selected aromatic tertiary amine moieties, and G is a linking group such as an arylene, cycloalkylene, or alkylene group of a carbon to carbon bond. In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural formula (HT1) and containing two triarylamine moieties is represented by structural formula (HT2):

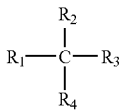
(HT2)

wherein:

$R_1$ and $R_2$ each independently represents a hydrogen atom, an aryl group, or an alkyl group or $R_1$ and $R_2$ together represent the atoms completing a cycloalkyl group; and $R_3$ and $R_4$ each independently represents an aryl group, which is in turn substituted with a diaryl substituted amino group, as indicated by structural formula (HT3):

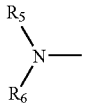
(HT3)

wherein:

$R_5$ and $R_6$ are independently selected aryl groups. In one embodiment, at least one of $R_5$ or $R_6$ contains a polycyclic fused ring structure, e.g., a naphthalene.

Another class of aromatic tertiary amines is the tetraaryldiamines. Desirable tetraaryldiamines include two diarylamino groups, such as indicated by formula (HT3), linked through an arylene group. Useful tetraaryldiamines include those represented by formula (HT4):

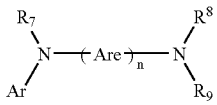
(HT4)

wherein:

each Are is an independently selected arylene group, such as a phenylene or anthracene moiety, n is an integer of from 1 to 4, and $R_1$, $R_2$, $R_3$, and $R_4$ are independently selected aryl groups. In a typical embodiment, at least one of $R_1$, $R_2$, $R_3$, and $R_4$ is a polycyclic fused ring structure, e.g., a naphthalene.

The various alkyl, alkylene, aryl, and arylene moieties of the foregoing structural formulae (HT1), (HT2), (HT3), (HT4) can each in turn be substituted. Typical substituents include alkyl groups, alkoxy groups, aryl groups, aryloxy groups, and halide such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, such as cyclopentyl, cyclohexyl, and cycloheptyl ring structures. The aryl and arylene moieties are usually phenyl and phenylene moieties.

The hole-transporting layer can be formed of a single tertiary amine compound or a mixture of such compounds. Specifically, one may employ a triarylamine, such as a triarylamine satisfying the formula (HT2), in combination with a tetraaryldiamine, such as indicated by formula (HT4). Illustrative of useful aromatic tertiary amines are the following:

1,1-Bis(4-di-p-tolylaminophenyl)cyclohexane (TAPC);
1,1-Bis(4-di-p-tolylaminophenyl)-4-phenylcyclohexane;
N,N,N',N'-tetraphenyl-4,4'''-diamino-1,1':4',1":4",1'''-quaterphenyl;
Bis(4-dimethylamino-2-methylphenyl)phenylmethane;
1,4-bis[2-[4-[N,N-di(p-tolyl)amino]phenyl]vinyl]benzene (BDTAPVB);
N,N,N',N'-Tetra-p-tolyl-4,4'-diaminobiphenyl;
N,N,N',N'-Tetraphenyl-4,4'-diaminobiphenyl;
N,N,N',N'-tetra-1-naphthyl-4,4'-diaminobiphenyl;
N,N,N',N'-tetra-2-naphthyl-4,4'-diaminobiphenyl;
N-Phenylcarbazole;
4,4'-Bis[N-(1-naphthyl)-N-phenylamino]biphenyl (NPB);
4,4'-Bis[N-(3-methylphenyl)-N-phenylamino]biphenyl (TPD);
4,4'-Bis[N-(1-naphthyl)-N-(2-naphthyl)amino]biphenyl (TNB);
4,4'-Bis[N-(1-naphthyl)-N-phenylamino]-p-terphenyl;
4,4'-Bis[N-(2-naphthyl)-N-phenylamino]biphenyl;
4,4'-Bis[N-(3-acenaphthenyl)-N-phenylamino]biphenyl;
1,5-Bis[N-(1-naphthyl)-N-phenylamino]naphthalene;
4,4'-Bis[N-(9-anthryl)-N-phenylamino]biphenyl;
4,4'-Bis[N-(1-anthryl)-N-phenylamino]-p-terphenyl;
4,4'-Bis[N-(2-phenanthryl)-N-phenylamino]biphenyl;
4,4'-Bis[N-(8-fluoranthenyl)-N-phenylamino]biphenyl;
4,4'-Bis[N-(2-pyrenyl)-N-phenylamino]biphenyl;
4,4'-Bis[N-(2-naphthacenyl)-N-phenylamino]biphenyl;
4,4'-Bis[N-(2-perylenyl)-N-phenylamino]biphenyl;
4,4'-Bis[N-(1-coronenyl)-N-phenylamino]biphenyl;
2,6-Bis(di-p-tolylamino)naphthalene;
2,6-Bis[di-(1-naphthyl)amino]naphthalene;
2,6-Bis[N-(1-naphthyl)-N-(2-naphthyl)amino]naphthalene;
N,N,N',N'-Tetra(2-naphthyl)-4,4"-diamino-p-terphenyl;
4,4'-Bis{N-phenyl-N-[4-(1-naphthyl)-phenyl]amino}biphenyl;
2,6-Bis[N,N-di(2-naphthyl)amino]fluorine;
4,4',4"-tris[(3-methylphenyl)phenylamino]triphenylamine (MTDATA);
N,N-bis[2,5-dimethyl-4-[(3-methylphenyl)phenylamino]phenyl]-2,5-dimethyl-N'-(3-methylphenyl)-N'-phenyl-1,4-benzenediamine;
4-(9H-carbazol-9-yl)-N,N-bis[4-(9H-carbazol-9-yl)phenyl]-benzenamine (TCTA);
4-(3-phenyl-9H-carbazol-9-yl)-N,N-bis[4(3-phenyl-9-carbazol-9-yl)phenyl]-benzenamine;
9,9'-(2,2'-dimethyl [1,1'-biphenyl]-4,4'-diyl)bis-9H-carbazole (CDBP);
9,9'-[1,1'-biphenyl]-4,4'-diylbis-9H-carbazole (CBP);
9,9'-(1,3-phenylene)bis-9H-carbazole (mCP);
9-[4-(9H-carbazol-9-yl)phenyl]-N,N-diphenyl-9H-carbazol-3-amine;
9,9'-(1,4-phenylene)bis[N,N-diphenyl-9H-carbazol-3-amine;

9-[4-(9H-carbazol-9-yl)phenyl]-N,N,N',N'-tetraphenyl-9H-carbazole-3,6-diamine.

Another class of useful hole-transporting materials includes polycyclic aromatic compounds as described in EP 1 009 041. Some hole-injecting materials described in EP 0 891 121 A1 and EP 1 029 909 A1, can also make useful hole-transporting materials. In addition, polymeric hole-transporting materials can be used including poly(N-vinylcarbazole) (PVK), polythiophenes, polypyrrole, polyaniline, and copolymers including poly(3,4-ethylenedioxythiophene)/poly(4-styrenesulfonate) also called PEDOT/PSS.

Exciton Blocking Layer (EBL)

As described previously, an optional exciton- or electron-blocking layer may be present between the HTL and the LEL (not shown in the FIGURE). Some suitable examples of such blocking layers are described in U.S. Ser. No. 11/016,108 of Marina E. Kondavova et al., filed Dec. 17, 2004 now U.S. Pat. No. 7,597,967.

Light-Emitting Layer (LEL)

The light-emitting layer has been described previously. The device may have more than one light-emitting layer. Additional light-emitting layers may include phosphorescent materials or fluorescent materials. The term "fluorescent" refers to a material that emits light from a singlet-excited state.

Fluorescent materials may be used in the same layer as the phosphorescent material, in adjacent layers, in adjacent pixels, or any combination. Care must be taken to select materials that will not adversely affect the performance of the phosphorescent materials of this invention. One skilled in the art will understand that concentrations and triplet energies of materials in the same layer as the phosphorescent material or in an adjacent layer must be appropriately set so as to prevent unwanted quenching of the phosphorescence.

As more fully described in U.S. Pat. Nos. 4,769,292 and 5,935,721, the light-emitting layer (LEL) of the organic EL element includes a luminescent fluorescent or phosphorescent material where electroluminescence is produced as a result of electron-hole pair recombination in this region. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. The emitting material is usually chosen from highly fluorescent dyes and phosphorescent compounds, e.g., transition metal complexes as described in WO 98/55561, WO 00/18851, WO 00/57676, and WO 00/70655. Emitting materials are typically incorporated at 0.01 to 10% by weight of the host material.

The host and emitting materials can be small non-polymeric molecules or polymeric materials such as polyfluorenes and polyvinylarylenes (e.g., poly(p-phenylenevinylene), PPV). In the case of polymers, small molecule emitting materials can be molecularly dispersed into a polymeric host, or the emitting materials can be added by copolymerizing a minor constituent into a host polymer.

An important relationship for choosing an emitting material is a comparison of the bandgap potential which is defined as the energy difference between the highest occupied molecular orbital and the lowest unoccupied molecular orbital of the molecule. For efficient energy transfer from the host to the emitting material, a necessary condition is that the band gap of the dopant is smaller than that of the host material. For phosphorescent emitters it is also important that the host triplet energy level be high enough to enable energy transfer from host to emitting material.

Host and emitting materials known to be of use include, but are not limited to, those disclosed in U.S. Pat. No. 4,768,292, U.S. Pat. No. 5,141,671, U.S. Pat. No. 5,150,006, U.S. Pat. No. 5,151,629, U.S. Pat. No. 5,405,709, U.S. Pat. No. 5,484,922, U.S. Pat. No. 5,593,788, U.S. Pat. No. 5,645,948, U.S. Pat. No. 5,683,823, U.S. Pat. No. 5,755,999, U.S. Pat. No. 5,928,802, U.S. Pat. No. 5,935,720, U.S. Pat. No. 5,935,721, and U.S. Pat. No. 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

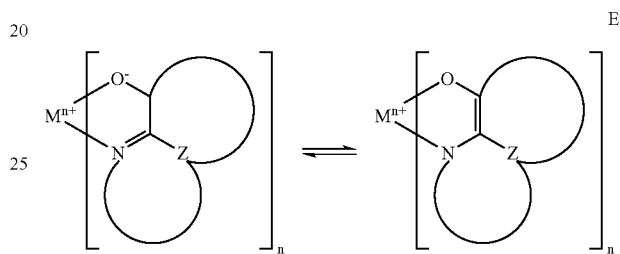

E wherein
  M represents a metal;
  n is an integer of from 1 to 4; and
  Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]
CO-2: Magnesium bisoxine [alias, bis(8-quinolinolato)magnesium(II)]
CO-3: Bis[benzo {f}-8-quinolinolato]zinc (II)
CO-4: Bis(2-methyl-8-quinolinolato)aluminum(III)-μ-oxo-bis(2-methyl-8-quinolinolato)aluminum(III)
CO-5: Indium trisoxine [alias, tris(8-quinolinolato)indium]
CO-6: Aluminum tris(5-methyloxine) [alias, tris(5-methyl-8-quinolinolato)aluminum(III)]
CO-7: Lithium oxine [alias, (8-quinolinolato)lithium(I)]
CO-8: Gallium oxine [alias, tris(8-quinolinolato)gallium (III)]
CO-9: Zirconium oxine [alias, tetra(8-quinolinolato)zirconium(IV)]

Derivatives of anthracene (Formula F) constitute one class of useful host materials capable of supporting electroluminescence, and are particularly suitable for light emission of wavelengths longer than 400 nm, e.g., blue, green, yellow, orange or red. Asymmetric anthracene derivatives as disclosed in U.S. Pat. No. 6,465,115 and WO 2004/018587 are also useful hosts.

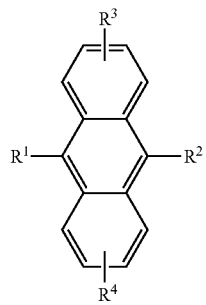

F wherein: $R^1$ and $R^2$ represent independently selected aryl groups, such as naphthyl, phenyl, biphenyl, triphenyl, anthracene.

$R^3$ and $R^4$ represent one or more substituents on each ring where each substituent is individually selected from the following groups:

Group 1: hydrogen, or alkyl of from 1 to 24 carbon atoms;
Group 2: aryl or substituted aryl of from 5 to 20 carbon atoms;
Group 3: carbon atoms from 4 to 24 necessary to complete a fused aromatic ring of anthracenyl; pyrenyl, or perylenyl;
Group 4: heteroaryl or substituted heteroaryl of from 5 to 24 carbon atoms as necessary to complete a fused heteroaromatic ring of furyl, thienyl, pyridyl, quinolinyl or other heterocyclic systems;
Group 5: alkoxylamino, alkylamino, or arylamino of from 1 to 24 carbon atoms; and
Group 6: fluorine or cyano.

A useful class of anthracenes are derivatives of 9,10-di-(2-naphthyl)anthracene (Formula G).

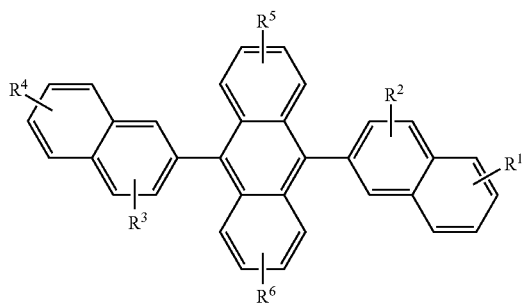

G wherein: $R^1$, $R^2$, $R^3$, $R^4$, $R^5$, and $R^6$ represent one or more substituents on each ring where each substituent is individually selected from the following groups:

Group 1: hydrogen, or alkyl of from 1 to 24 carbon atoms;
Group 2: aryl or substituted aryl of from 5 to 20 carbon atoms;
Group 3: carbon atoms from 4 to 24 necessary to complete a fused aromatic ring of anthracenyl; pyrenyl, or perylenyl;
Group 4: heteroaryl or substituted heteroaryl of from 5 to 24 carbon atoms as necessary to complete a fused heteroaromatic ring of furyl, thienyl, pyridyl, quinolinyl or other heterocyclic systems;
Group 5: alkoxylamino, alkylamino, or arylamino of from 1 to 24 carbon atoms; and
Group 6: fluorine or cyano.

Illustrative examples of anthracene materials for use in a light-emitting layer include: 2-(4-methylphenyl)-9,10-di-(2-naphthyl)-anthracene; 9-(2-naphthyl)-10-(1,1'-biphenyl)-anthracene; 9,10-bis[4-(2,2-diphenylethenyl)phenyl]-anthracene;

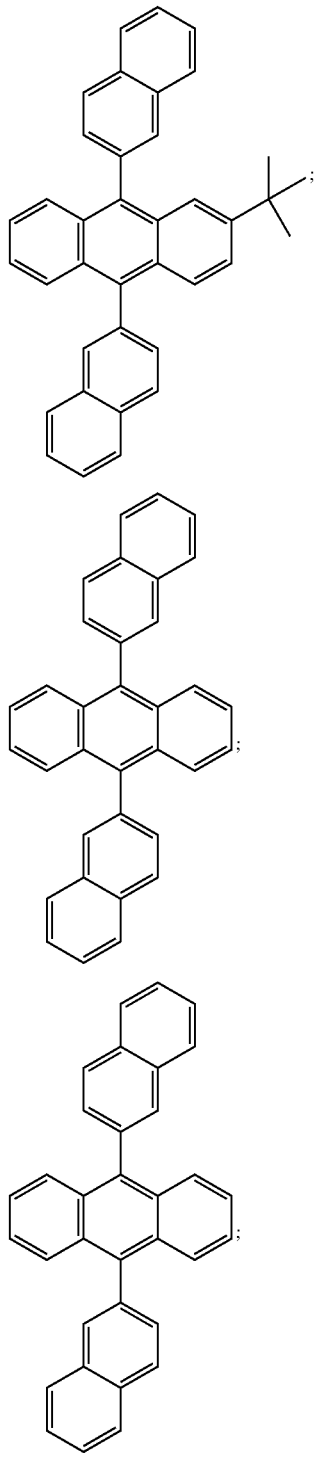

-continued

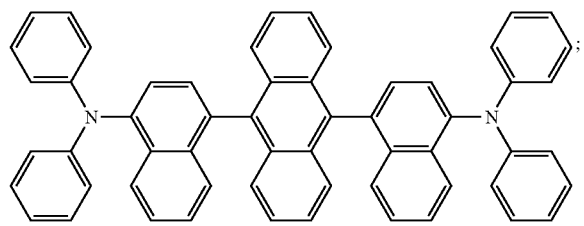

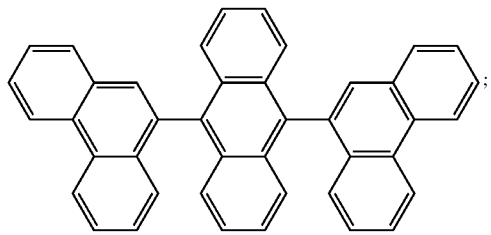

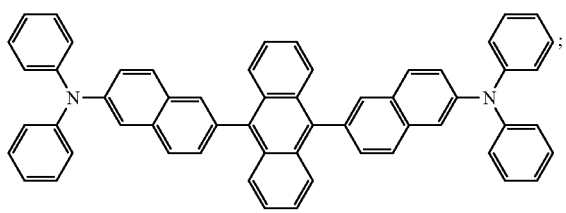

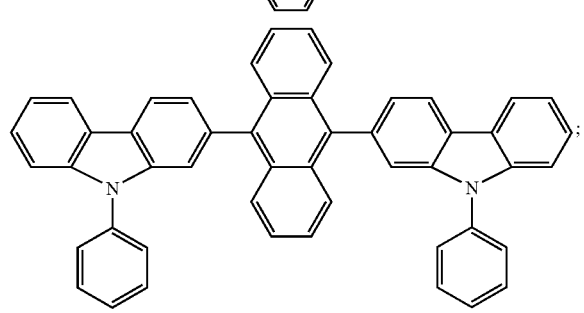

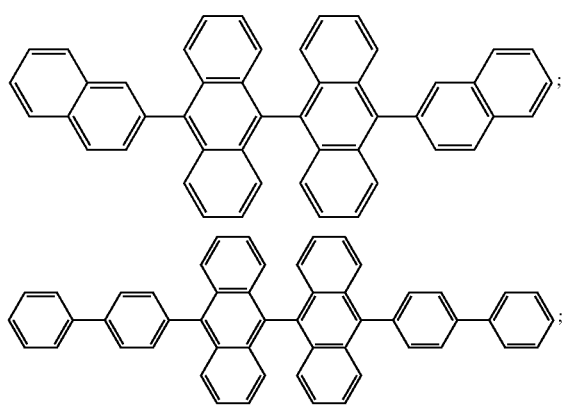

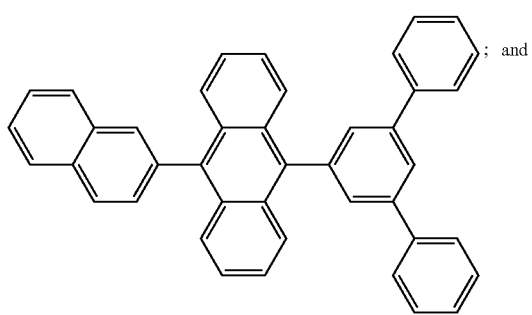
; and

-continued

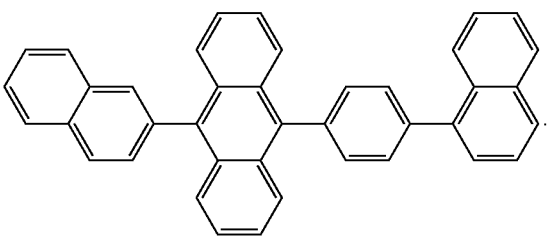

Distyrylarylene derivatives are also useful hosts, as described in U.S. Pat. No. 5,121,029. Carbazole derivatives are particularly useful hosts for phosphorescent emitters.

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrilium and thiapyrilium compounds, fluorene derivatives, periflanthene derivatives, indenoperylene derivatives, bis(azinyl)amine boron compounds, bis(azinyl)methane compounds, and carbostyryl compounds. Illustrative examples of useful materials include, but are not limited to, the following:

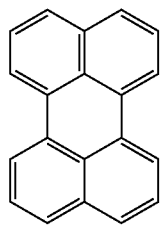

L1

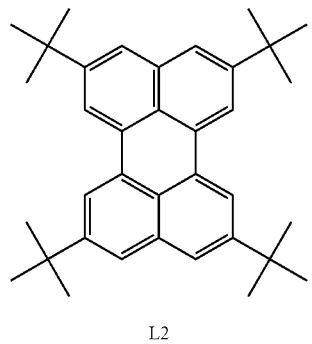 [SMILES: CC(C)(C)c1cc2cc(C(C)(C)C)cc3c4cc(C(C)(C)C)cc5cc(C(C)(C)C)cc(c(c1)c23)c54]

L2

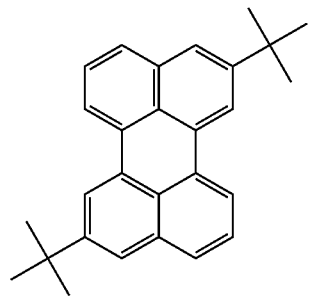

L3

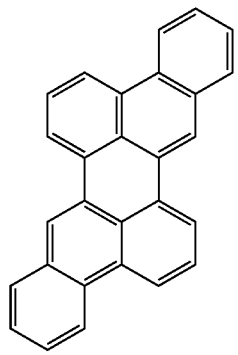
L4
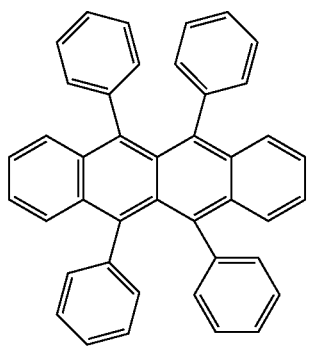
L5
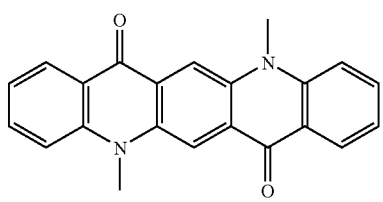
L6
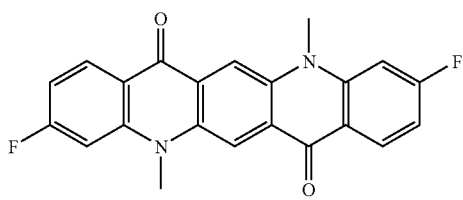
L7
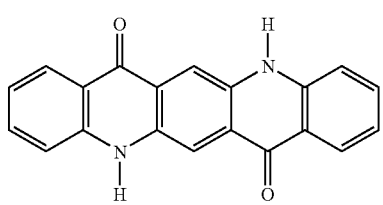
L8
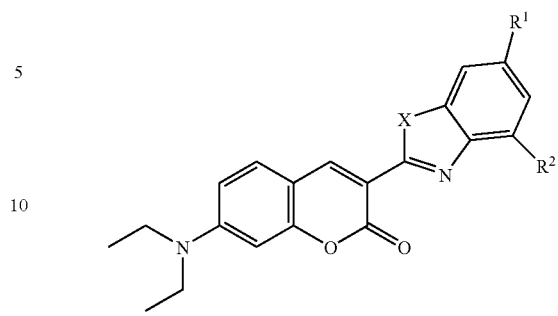
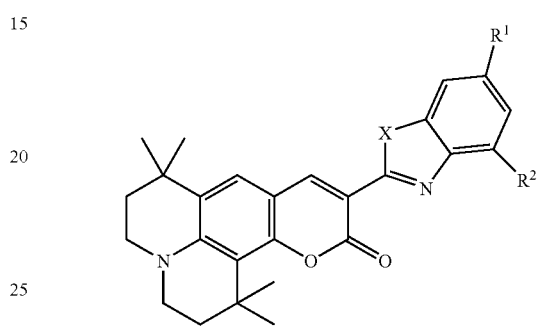
|     | X | R1     | R2     |
|-----|---|--------|--------|
| L9  | O | H      | H      |
| L10 | O | H      | Methyl |
| L11 | O | Methyl | H      |
| L12 | O | Methyl | Methyl |
| L13 | O | H      | t-butyl |
| L14 | O | t-butyl | H     |
| L15 | O | t-butyl | t-butyl |
| L16 | S | H      | H      |
| L17 | S | H      | Methyl |
| L18 | S | Methyl | H      |
| L19 | S | Methyl | Methyl |
| L20 | S | H      | t-butyl |
| L21 | S | t-butyl | H     |
| L22 | S | t-butyl | t-butyl |
| L23 | O | H      | H      |
| L24 | O | H      | Methyl |
| L25 | O | Methyl | R      |
| L26 | O | Methyl | Methyl |
| L27 | O | H      | t-butyl |
| L28 | O | t-butyl | H     |
| L29 | O | t-butyl | t-butyl |
| L30 | S | H      | H      |
| L31 | S | H      | Methyl |
| L32 | S | Methyl | H      |
| L33 | S | Methyl | Methyl |
| L34 | S | H      | t-butyl |
| L35 | S | t-butyl | H     |
| L36 | S | t-butyl | t-butyl |
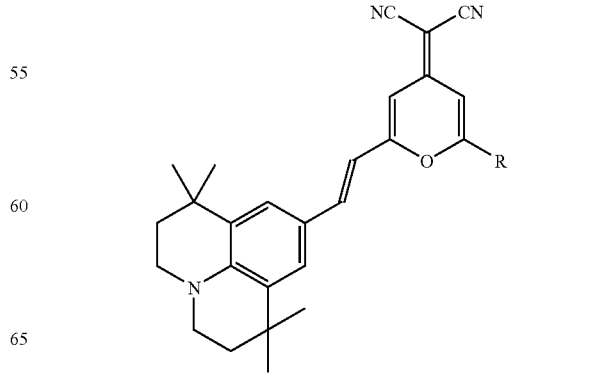

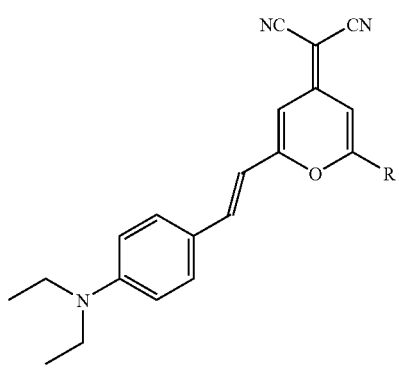
| | R |
|---|---|
| L37 | phenyl |
| L38 | methyl |
| L39 | t-butyl |
| L40 | mesityl |
| L41 | phenyl |
| L42 | methyl |
| L43 | t-butyl |
| L44 | mesityl |
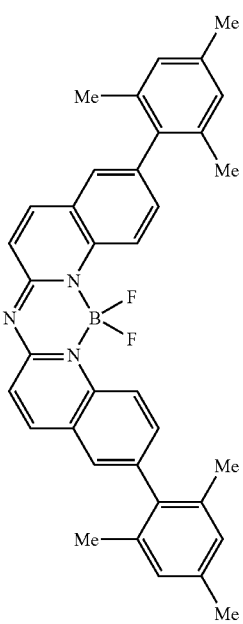
L46
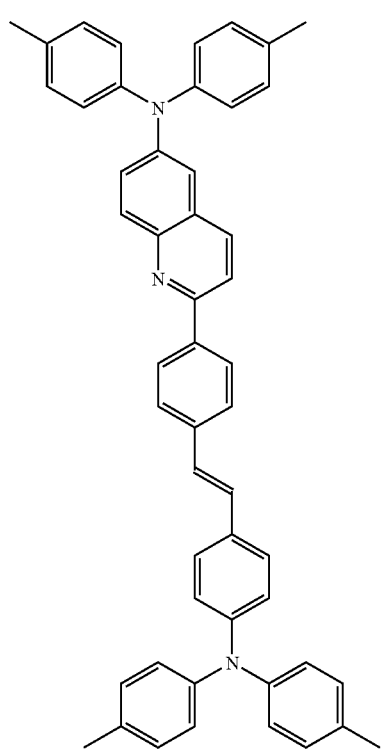
L45
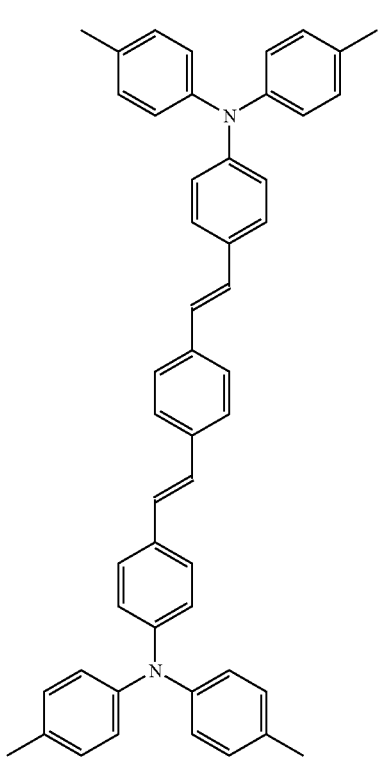
L47

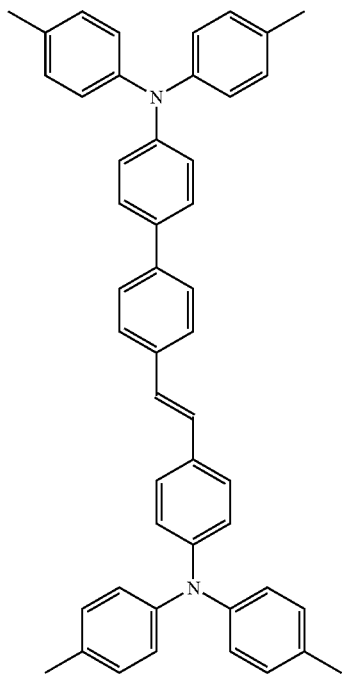

L48

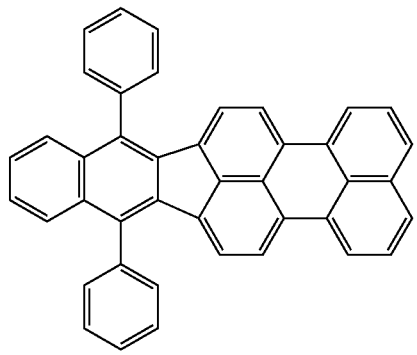

L49

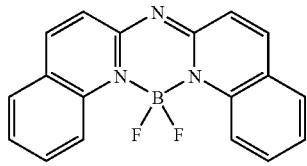

L50

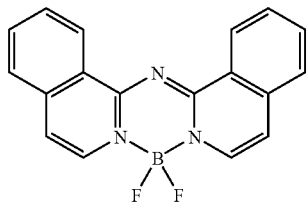

L51

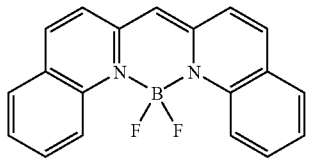

L52

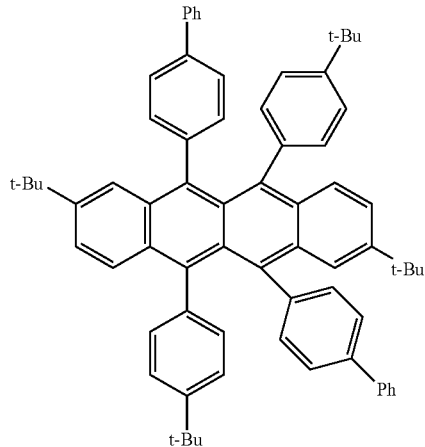

L53

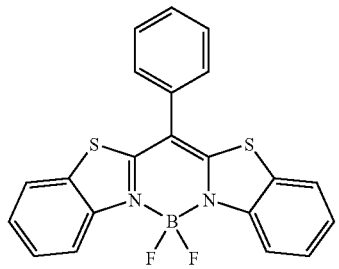

L54

In addition to the phosphorescent materials of Formula (1), additional phosphorescent materials may be present in the same or a different layer. Examples of other phosphorescent materials are reported in WO 00/57676, WO 00/70655, WO 01/41512, WO 02/15645, U.S. 2003/0017361, WO 01/93642, WO 01/39234, U.S. Pat. No. 6,458,475, WO 02/071813, U.S. Pat. No. 6,573,651, U.S. 2002/0197511, WO 02/074015, U.S. Pat. No. 6,451,455, U.S. 2003/0072964, U.S. 2003/0068528, U.S. Pat. No. 6,413,656, U.S. Pat. No. 6,515,298, U.S. Pat. No. 6,451,415, U.S. Pat. No. 6,097,147, U.S. 2003/0124381, U.S. 2003/0059646, U.S. 2003/0054198, EP 1 239 526, EP 1 238 981, EP 1 244 155, U.S. 2002/0100906, U.S. 2003/0068526, U.S. 2003/0068535, JP 2003073387, JP 2003073388, U.S. 2003/0141809, U.S. 2003/0040627, JP 2003059667, JP 2003073665, and U.S. 2002/0121638.

The emission wavelengths of cyclometallated Ir(III) complexes of the type $IrL_3$ and $IrL_2L'$, such as the green-emitting fac-tris(2-phenylpyridinato-N,$C^{2'}$)Iridium(III) and bis(2-phenylpyridinato-N,$C^{2'}$)Iridium(III)(acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-N,C$^{3'}$)Iridium(III)(acetylacetonate) and tris(2-phenylisoquinolinato-N,C)Iridium(III). A blue-emitting example is bis(2-(4,6-diflourophenyl)-pyridinato-N,C$^{2'}$)Iridium(III)(picolinate).

Other important phosphorescent materials include cyclometallated Pt(II) complexes such as cis-bis(2-phenylpyridinato-N,C$^{2'}$)platinum(II), cis-bis(2-(2'-thienyl)pyridinato-N, C$^{3'}$) platinum(II), cis-bis(2-(2'-thienyl)quinolinato-N,C$^{5'}$) platinum(II), or (2-(4,6-diflourophenyl)pyridinato-NC2') platinum (II) acetylacetonate. Pt(II) porphyrin complexes such as 2,3,7,8,12,13,17,18-octaethyl-21H, 23H-porphine platinum(II) are also useful phosphorescent materials.

Still other examples of useful phosphorescent materials include coordination complexes of the trivalent lanthanides such as Tb$^{3+}$ and Eu$^{3+}$ (J. Kido et al, *Appl. Phys. Lett.*, 65, 2124 (1994))

Hole-Blocking Layer (HBL)

As described previously, in addition to suitable hosts and transporting materials, an OLED device according to the invention may also include at least one hole-blocking layer 110 placed between the electron-transporting layer 111 and the light-emitting layer 109 to help confine the excitons and recombination events to the light-emitting layer comprising hosts or co-hosts and a phosphorescent emitter. In this case, there should be an energy barrier for hole migration from hosts or co-hosts into the hole-blocking layer, while electrons should pass readily from the hole-blocking layer into the light-emitting layer comprising hosts or co-host materials and a phosphorescent emitter. The first requirement entails that the ionization potential of the hole-blocking layer 110 be larger than that of the light-emitting layer 109, desirably by 0.2 eV or more. The second requirement entails that the electron affinity of the hole-blocking layer 110 not greatly exceed that of the light-emitting layer 109, and desirably be either less than that of light-emitting layer or not exceed that of the light-emitting layer by more than about 0.2 eV.

When used with an electron-transporting layer whose characteristic luminescence is green, such as an Alq-containing electron-transporting layer as described below, the requirements concerning the energies of the highest occupied molecular orbital (HOMO) and lowest unoccupied molecular orbital (LUMO) of the material of the hole-blocking layer frequently result in a characteristic luminescence of the hole-blocking layer at shorter wavelengths than that of the electron-transporting layer, such as blue, violet, or ultraviolet luminescence. Thus, it is desirable that the characteristic luminescence of the material of a hole-blocking layer be blue, violet, or ultraviolet. It is further desirable that the triplet energy of the hole-blocking material be greater than that of the phosphorescent material. Suitable hole-blocking materials are described in WO 00/70655A2, WO 01/41512 and WO 01/93642 A1. Two examples of useful hole-blocking materials are bathocuproine (BCP) and bis(2-methyl-8-quinolinolato)(4-phenylphenolato)aluminum(III) (BAlq). The characteristic luminescence of BCP is in the ultraviolet, and that of BAlq is blue. Metal complexes other than BAlq are also known to block holes and excitons as described in U.S. 20030068528. When a hole-blocking layer is used, its thickness can be between 2 and 100 nm and suitably between 5 and 10 mm.

Electron-Transporting Layer (ETL)

The electron transporting material deposited in said electron transporting layer between the cathode and the light emitting layer may be the same or different from an electron transporting hosts or co-host material. The electron transporting layer may include more than one electron transporting compound, deposited as a blend or divided into separate layers.

Preferred thin film-forming materials for use in constructing the electron transporting layer of the organic EL devices of this invention are metal-chelated oxinoid compounds, including chelates of oxine itself (also commonly referred to as 8-quinolinol or 8-hydroxyquinoline). Such compounds help to inject and transport electrons, exhibiting high levels of performance, and are readily fabricated in the form of thin films. Exemplary of contemplated oxinoid compounds are those satisfying structural formula (ET1) below:

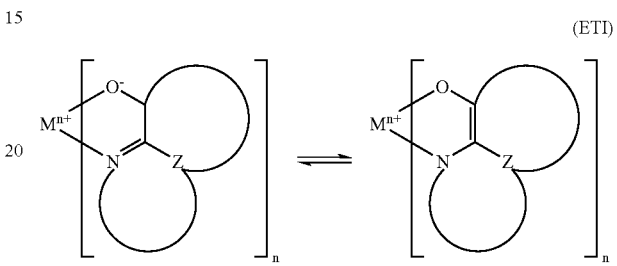

(ET1)

wherein:

M represents a metal;

n is an integer of from 1 to 4; and

Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)];

CO-2: Magnesium bisoxine [alias, bis(8-quinolinolato)magnesium(II)];

CO-3: Bis[benzo{f}-8-quinolinolato]zinc (II);

CO-4: Bis(2-methyl-8-quinolinolato)aluminum(III)-μ-oxo-bis(2-methyl-8-quinolinolato)aluminum(III);

CO-5: Indium trisoxine [alias, tris(8-quinolinolato)indium];

CO-6: Aluminum tris(5-methyloxine) [alias, tris(5-methyl-8-quinolinolato)aluminum(III)];

CO-7: Lithium oxine [alias, (8-quinolinolato)lithium(I)];

CO-8: Gallium oxine [alias, tris(8-quinolinolato)gallium (III)];

CO-9: Zirconium oxine [alias, tetra(8-quinolinolato)zirconium(IV)].

Other electron transporting materials suitable for use in the electron transporting layer include various butadiene derivatives as disclosed in U.S. Pat. No. 4,356,429 and various heterocyclic optical brighteners as described in U.S. Pat. No.

4,539,507. Benzazoles satisfying structural formula (ET2) are also useful electron transporting materials:

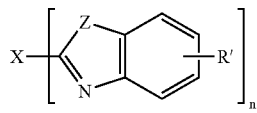

wherein:

n is an integer of 3 to 8;

Z is O, NR or S; and

R and R' are individually hydrogen; alkyl of from 1 to 24 carbon atoms, for example, propyl, t-butyl, heptyl, and the like; aryl or hetero-atom substituted aryl of from 5 to 20 carbon atoms for example phenyl and naphthyl, furyl, thienyl, pyridyl, quinolinyl and other heterocyclic systems; or halo such as chloro, fluoro; or atoms necessary to complete a fused aromatic ring; and X is a linkage unit consisting of carbon, alkyl, aryl, substituted alkyl, or substituted aryl, which conjugately or unconjugately connects the multiple benzazoles together. An example of a useful benzazole is 2,2',2"-(1,3,5-phenylene)tris [1-phenyl-1H-benzimidazole] (TPBI) disclosed in Shi et al. in U.S. Pat. No. 5,766,779.

Other electron-transporting materials suitable for use in the electron-transporting layer 111 include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials. Further useful materials are silacyclopentadiene derivatives described in EP 1,480,280; EP 1,478,032; and EP 1,469,533. Substituted 1,10-phenanthroline compounds such as

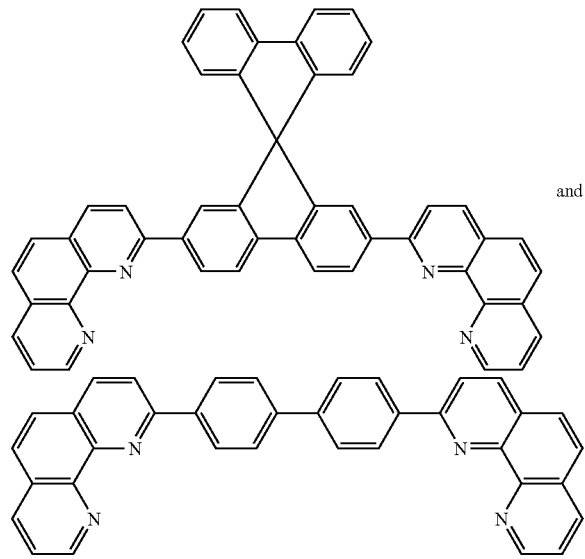

and are disclosed in JP2003-115387; JP2004-311184; JP2001-267080; and WO2002-043449. Pyridine derivatives are described in JP2004-200162 as useful electron transporting materials.

In one embodiment, the electron-transporting layer includes a mixture of materials such as those described by W. Begley et al. in U.S. Ser. No. 11/076,821 filed Mar. 10, 2005 (now abandoned); U.S. Ser. No. 11/077,218 filed Mar. 10, 2005 (published as US 2006/0204784); and U.S. Ser. No. 11/116,096 filed Apr. 27, 2005 (published as US 2006/0246315), the disclosures of which are incorporated herein by reference.

If both a hole-blocking layer and an electron-transporting layer 111 are used, electrons should pass readily from the electron-transporting layer 111 into the hole-blocking layer. Therefore, the electron affinity of the electron-transporting layer 111 should not greatly exceed that of the hole-blocking layer. Desirably, the electron affinity of the electron-transporting layer should be less than that of the hole-blocking layer or not exceed it by more than about 0.2 eV.

If an electron-transporting layer is used, its thickness may be between 2 and 100 nm and suitably between 5 and 20 nm.

Electron-Injecting Layer (EIL)

Electron-injecting layers (not shown in the FIGURE), when present, include those described in U.S. Pat. Nos. 5,608,287; 5,776,622; 5,776,623; 6,137,223; and 6,140,763, the disclosures of which are incorporated herein by reference. An electron-injecting layer generally consists of a material having a work function less than 4.0 eV. A thin-film containing low work-function alkaline metals or alkaline earth metals, such as Li, Cs, Ca, Mg can be employed. In addition, an organic material doped with these low work-function metals can also be used effectively as the electron-injecting layer. Examples are Li- or Cs-doped Alq. In one suitable embodiment the electron-injecting layer includes LiF. In practice, the electron-injecting layer is often a thin layer deposited to a suitable thickness in a range of 0.1-3.0 nm.

Cathode

When light emission is viewed solely through the anode 103, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, as disclosed in U.S. Pat. No. 6,013,384, is another example of a useful EIL. Other useful cathode material sets include, but are not limited to, those disclosed in U.S. Pat. Nos. 5,059,861, 5,059,862, and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. No. 4,885,211, U.S. Pat. No. 5,247,190, JP 3,234, 963, U.S. Pat. No. 5,703,436, U.S. Pat. No. 5,608,287, U.S. Pat. No. 5,837,391, U.S. Pat. No. 5,677,572, U.S. Pat. No. 5,776,622, U.S. Pat. No. 5,776,623, U.S. Pat. No. 5,714,838, U.S. Pat. No. 5,969,474, U.S. Pat. No. 5,739,545, U.S. Pat. No. 5,981,306, U.S. Pat. No. 6,137,223, U.S. Pat. No. 6,140, 763, U.S. Pat. No. 6,172,459, EP 1 076 368, U.S. Pat. No. 6,278,236, and U.S. Pat. No. 6,284,393. Cathode materials are typically deposited by any suitable methods such as evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Other Common Organic Layers and Device Architecture

In some instances, layers 109 and 111 can optionally be collapsed into a single layer that serves the function of supporting both light emission and electron transportation. It also known in the art that emitting dopants may be added to the hole-transporting layer, which may serve as a host. Multiple dopants may be added to one or more layers in order to create a white-emitting OLED, for example, by combining blue- and yellow-emitting materials, cyan- and red-emitting materials, or red-, green-, and blue-emitting materials. White-emitting devices are described, for example, in EP 1 187 235, EP 1 182 244, U.S. Pat. No. 5,683,823, U.S. Pat. No. 5,503,910, U.S. Pat. No. 5,405,709, and U.S. Pat. No. 5,283,182, U.S. 20020186214, U.S. 20020025419,U.S. 20040009367, and U.S. 6627333.

Additional layers such as exciton, electron and hole-blocking layers as taught in the art may be employed in devices of this invention. Hole-blocking layers are commonly used to improve efficiency of phosphorescent emitter devices, for example, as in U.S. 20020015859, WO 00/70655A2, WO 01/93642A1, U.S. 20030068528 and U.S. 20030175553 A1.

This invention may be used in so-called stacked device architecture, for example, as taught in U.S. Pat. No. 5,703,436 and U.S. Pat. No. 6,337,492.

Deposition of Organic Layers

The organic materials mentioned above are suitably deposited through a vapor-phase method such as sublimation, but can be deposited from a fluid, for example, from a solvent with an optional binder to improve film formation. If the material is a polymer, solvent deposition is useful but other methods can be used, such as sputtering or thermal transfer from a donor sheet. The material to be deposited by sublimation can be vaporized from a sublimation "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimation boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851,709 and 6,066,357) and inkjet method (U.S. Pat. No. 6,066,357).

One preferred method for depositing the materials of the present invention is described in US 2004/0255857 and U.S. Ser. No. 10/945,941 (now U.S. Pat. No. 7,288,286) where different source evaporators are used to evaporate each of the materials of the present invention. A second preferred method involves the use of flash evaporation where materials are metered along a material feed path in which the material feed path is temperature controlled. Such a preferred method is described in the following co-assigned patent applications: U.S. Ser. No. 10/784,585 (U.S. Pat. No. 7,232,588); U.S. Ser. No. 10/805,980 (U.S. Pat. No. 7,238,389); U.S. Ser. No. 10/945,940 (U.S. Pat. No. 7,288,285); U.S. Ser. No. 10/945,941 (U.S. Pat. No. 7,288,286); U.S. Ser. No. 11/050,924 (U.S. Pat. No. 7,625,601); and U.S. Ser. No. 11/050,934 (U.S. Pat. No. 7,165,340). Using this second method, each material may be evaporated using different source evaporators or the solid materials may be mixed prior to evaporation using the same source evaporator.

Encapsulation

Most OLED devices are sensitive to moisture or oxygen, or both, so they are commonly sealed in an inert atmosphere such as nitrogen or argon. In sealing an OLED device in an inert environment, a protective cover can be attached using an organic adhesive, a metal solder, or a low melting temperature glass. Commonly, a getter or desiccant is also provided within the sealed space. Useful getters and desiccants include, alkali and alkaline metals, alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

Optical Optimization

OLED devices of this invention can employ various well-known optical effects in order to enhance its properties if desired. This includes optimizing layer thicknesses to yield maximum light transmission, providing dielectric mirror structures, replacing reflective electrodes with light-absorbing electrodes, providing anti glare or anti-reflection coatings over the display, providing a polarizing medium over the display, or providing colored, neutral density, or color conversion filters in functional relationship with the light emitting areas of the display. Filters, polarizers, and anti-glare or anti-reflection coatings can also be provided over a cover or as part of a cover.

The OLED device may have a microcavity structure. In one useful example, one of the metallic electrodes is essentially opaque and reflective; the other one is reflective and semi-transparent. The reflective electrode is preferably selected from Au, Ag, Mg, Ca, or alloys thereof. Because of the presence of the two reflecting metal electrodes, the device has a microcavity structure. The strong optical interference in this structure results in a resonance condition. Emission near the resonance wavelength is enhanced and emission away from the resonance wavelength is depressed. The optical path length can be tuned by selecting the thickness of the organic layers or by placing a transparent optical spacer between the electrodes. For example, an OLED device of this invention can have ITO spacer layer placed between a reflective anode and the organic EL media, with a semitransparent cathode over the organic EL media.

The entire contents of the patents and other publications referred to in this specification are incorporated herein by reference.

Embodiments of the invention may provide advantageous features such as higher luminous yield, lower drive voltage, and higher power efficiency, longer operating lifetimes or ease of manufacture. Embodiments of devices useful in the invention can provide a wide range of hues including those useful in the emission of white light (directly or through filters to provide multicolor displays). Embodiments of the invention can also provide an area lighting device.

The invention and its advantages are further illustrated by the specific examples that follow. Unless otherwise specified, the term "percentage" or "percent" and the symbol "%" of a material indicate the volume percent of the material in the layer in which it is present.

Example 1

Synthesis of Inv-1, fac-tris(2-phenylquinazolinato-N, C2')iridium(III)

$K_3IrBr_6$ (2.80 g, 3.55 mmol) was placed in a 200 mL round bottom flask with 45 mL of 2-ethoxyethanol, 15 mL water, and 2-phenylquinazoline (8.87 mmol). The mixture was freeze-thaw degassed, and then refluxed for 4 h under nitrogen atmosphere during which time an orange precipitate appeared. After cooling, the precipitate was collected by filtration, washed with 1N HBr(aq), then water, then ethanol, and dried to yield orange tetrakis(2-phenylquinazolinato-N,$C^{2'}$)(µ-dibromo)diiridium(III) (2.29 g, 94% yield based on iridium).

Then tetrakis(2-phenylquinazolinato-N,$C^{2'}$)(µ-dibromo)diiridium(III) (0.85 g, 1.245 mmol) and silver tetrafluoroborate (0.27 g) were placed in a 100-mL round-bottomed flask. Acetonitrile (30 mL) was added and the mixture was freeze-thaw degassed, and then refluxed for 3 h under nitrogen atmosphere. After cooling, the yellow solution was filtered thru celite filter aid to remove white insoluble material and the solvent was removed under vacuum. A yellow powder was collected, and dried to afford [bis(acetonitrile)bis(2-phenylquinazolinato-N,$C^{2'}$)iridium(III)]tetrafluoroborate (0.953 g, 99% based on iridium). Analysis by $H^1$ NMR spectroscopy and mass spectrometry confirmed that this material was bis(acetonitrile)bis[(2-phenylpyridinato-N,$C^{2'}$)]iridium(III) tetrafluoroborate.

Next, [bis(acetonitrile)bis(2-phenylquinazolinato-N,$C^{2'}$)iridium(III)]tetrafluoroborate (0.615 g, 0.797 mmol) and 2-phenylquinazoline (0.71 g) was placed in a 100-mL round-bottomed flask with 2-ethoxyethanol (30 mL). The mixture was freeze-thaw degassed, and then refluxed for 18 h under nitrogen atmosphere during which time a bright orange precipitate appeared. After cooling, the precipitate was collected by filtration, washed with ethanol and water and dried to afford fac-tris(2-phenylquinazolinato-N,$C^{2'}$)iridium(III) (0.433 g, 67.3% yield). Analysis by electrospray mass spectrometry (M+observed 807 amu) and 1H nmr spectroscopy confirmed the identity of the product.

Example 2

Synthesis of Inv-2, of fac-tris(4-phenylquinazolinato-N,$C^{2'}$)iridium(III)

$K_3IrBr_6$ (2.755 g, 3.49 mmol) was placed in a 125 mL round bottom flask with 39 mL of 2-ethoxyethanol, 13 mL water, and 4-phenylquinazoline (1.80 g, 8.73 mmol). The mixture was freeze-thaw degassed, and then refluxed for 4 h under nitrogen atmosphere during which time a dark red precipitate appeared. After cooling, the precipitate was collected by filtration, washed with methanol and ligroin, and dried to yield dark red tetrakis(4-phenylquinazolinato-N,$C^{2'}$)(µ-dibromo)diiridium(III) (2.265 g, 95% yield based on iridium).

Next, tetrakis(4-phenylquinazolinato-N,$C^{2'}$)(µ-dibromo)diiridium(III) (0.696 g, 1.02 mmol) and silver tetrafluoroborate (0.218 g) were placed in a 100-mL, round-bottom flask. Acetonitrile (30 mL) was added and the mixture was freeze-thaw degassed, and then refluxed for 3 h under nitrogen atmosphere. After cooling, the red-orange solution was filtered thru celite filter aid to remove white insoluble material and then the solvent was removed under vacuum. A red-orange was collected, and dried to afford [bis(acetonitrile)bis(4-phenylquinazolinato-N,$C^{2'}$)iridium(III)]tetrafluoroborate (0.759 g, 96% based on iridium). Analysis by $H^1$ NMR spectroscopy and mass spectrometry confirmed that this material was bis(acetonitrile)bis[(4-phenylpyridinato-N,$C^{2'}$)]iridium(III) tetrafluoroborate.

Then [bis(acetonitrile)bis(4-phenylquinazolinato-N,$C^{2'}$)iridium(III)]tetrafluoroborate (0.497 g, 0.644 mmol) and 4-phenylquinazoline (0.53 g) was placed in a 100-mL round-bottom flask with 2-ethoxyethanol (30 mL). The mixture was freeze-thaw degassed, and then refluxed for 18 h under nitrogen atmosphere during which time a dark red precipitate appeared. After cooling, the precipitate was collected by filtration, washed with ethanol and water and dried to afford fac-tris(4-phenylquinazolinato-N,$C^{2'}$)iridium(III) (0.375 g, 72% yield). Analysis by electrospray mass spectrometry (M+observed 807 amu) and $^1$H nmr spectroscopy confirmed the identity of the product.

Example 3

Fabrication of Device 1-1 Through 1-3

An EL device (1-1) satisfying the requirements of the invention was constructed in the following manner:

A glass substrate coated with an 85 nm layer of indium-tin oxide (ITO) as the anode was sequentially ultrasonicated in a commercial detergent, rinsed in deionized water, degreased in toluene vapor and exposed to oxygen plasma for about 1 min.

a) Over the ITO was deposited a 1 nm fluorocarbon (CFx) hole-injecting layer (HIL) by plasma-assisted deposition of $CHF_3$.

b) A hole-transporting layer (HTL) of N,N'-di-1-naphthalenyl-N,N'-diphenyl-4,4'-diaminobiphenyl (NPB) having a thickness of 150 nm was then evaporated from a tantalum boat.

c) A 35 nm LEL comprised of CBP (4,4'-N,N'-dicarbazole-biphenyl) and 4 wt % of the phosphorescent dopant Inv-1 were then deposited onto the hole-transporting layer. These materials were also evaporated from graphite boats.

d) A 10 nm hole blocking layer of bis(2-methyl-8-quinolinolato)$_2$(4-phenyl-phenolato)aluminum(III) (BAlq) was deposited onto the LEL. This material was also evaporated from a graphite boat.

e) A 40 nm electron-transporting layer (ETL) of tris(8-quinolinolato)aluminum (III) ($Alq_3$) was then deposited onto the light-emitting layer. This material was also evaporated from a graphite boat.

f) On top of the $Alq_3$ layer was deposited a 220 nm cathode formed of a 10:1 volume ratio of Mg and Ag.

The above sequence completed the deposition of the EL device. The device was then hermetically packaged in a dry glove box for protection against ambient environment. Device 1-2 and 1-3 were constructed in exactly the same manner as Device 1-1, except the level of Inv-1 was 6% and 8% respectively.

The cells thus formed were tested at 20 mA/cm$^2$ constant current for efficiency in the form of luminance yield (Cd/A) and radiant yield (W/A) where radiant yield is the radiant flux (in watts) produced by the device per amp of input current, where radiant flux is the light energy produced by the device per unit time. Testing also determined the output color, reported in CIEx, CIEy (Commission Internationale de L'Eclairage) coordinates and drive voltage. The results are listed in Table 1a and 1b.

The stability of the devices was also measured by operating the devices for 430 hrs at a current density of 20 mA/cm$^2$ and ambient temperature (~23° C.). The percent of luminance remaining after this time period relative to the initial luminance is listed in Table 1b as a percentage.

TABLE 1a

Testing data for Devices 1-1, 1-2, 1-3.

| Device | Inv-1 Level (%) | Color CIEx,y | Emission $\lambda_{max}$ (nm) | Luminance Yield (cd/A)[1] |
|---|---|---|---|---|
| 1-1 | 4 | 0.548,0.424 | 603 | 4.66 |
| 1-2 | 6 | 0.561,0.415 | 608 | 4.50 |
| 1-3 | 8 | 0.563,0.413 | 610 | 4.17 |

[1] at 20 mA/CM$^2$

TABLE 1b

Testing data for Devices 1-1, 1-2, 1-3.

| Device | Inv-1 Level (%) | Drive Voltage (V)[1] | Radiant Yield | Stability[2] (%) |
|---|---|---|---|---|
| 1-1 | 4 | 11.4 | 0.051 | 80.2% |
| 1-2 | 6 | 11.2 | 0.053 | 79.3% |
| 1-3 | 8 | 10.6 | 0.051 | 78.3% |

[1] at 20 mA/CM$^2$
[2] Percent luminance remaining after 430 hours of operation.

From the data presented in Table 1a and 1b, it can be seen that the devices according to the invention provide high luminance yield with high color purity and good stability.

Example 4

Fabrication of Device 2-1 Through 2-3

Device 2-1, 2-2, and 2-3 were fabricated in exactly the same manner as Device 1-1, 1-2, and 1-3 described above, except Inv-1 was replaced with Inv-2 in each case. The devices were tested in the same manner as those in Example 3 and the results are listed in Table 2a and 2b.

TABLE 2a

Testing data for Devices 2-1, 2-2, 2-3.

| Device | Inv-2 Level (%) | Color CIEx,y | Emission $\lambda_{max}$ (nm) | Luminance Yield (cd/A)[1] |
|---|---|---|---|---|
| 2-1 | 4 | 0.577,0.388 | 634 | 3.38 |
| 2-2 | 6 | 0.580,0.385 | 637 | 3.15 |
| 2-3 | 8 | 0.583,0.383 | 639 | 3.20 |

[1] at 20 mA/CM$^2$

TABLE 2b

Testing data for Devices 2-1, 2-2, 2-3.

| Device | Inv-2 Level (%) | Drive Voltage (V)[1] | Radiant Yield | Stability[2] (%) |
|---|---|---|---|---|
| 2-1 | 4 | 11.2 | 0.061 | 80.2% |
| 2-2 | 6 | 11.2 | 0.062 | 79.3% |
| 2-3 | 8 | 10.6 | 0.065 | 78.3% |

[1] at 20 mA/CM$^2$
[2] Percent luminance remaining after 430 hours of operation.

As can be seen from Table 2a and 2b, devices prepared according to the invention provide high luminance yield with high color purity and good stability.

Example 5

Fabrication of Device 3-1 Through 3-6

EL devices satisfying the requirements of the invention were constructed in the following manner:

A glass substrate coated with an 85 nm layer of indium-tin oxide (ITO) as the anode was sequentially ultrasonicated in a commercial detergent, rinsed in deionized water, degreased in toluene vapor and exposed to oxygen plasma for about 1 min.

a) Over the ITO was deposited a 1 nm fluorocarbon (CFx) hole-injecting layer (HIL) by plasma-assisted deposition of $CHF_3$.

b) A hole-transporting layer (HTL) of N,N'-di-1-naphthalenyl-N,N'-diphenyl-4,4'-diaminobiphenyl (NPB) having a thickness of 150 nm was then evaporated from a tantalum boat.

c) A 35 nm LEL comprised of the co-hosts PH-10 and NPB and the phosphorescent dopant Inv-2 were then deposited onto the hole-transporting layer. See Table 3a for the levels of each of these components. These materials were also evaporated from graphite boats.

d) A 10 nm hole-blocking layer of PH-10 was deposited onto the LEL.

e) A 40 nm electron-transporting layer (ETL) of tris(8-quinolinolato)aluminum (III) ($Alq_3$) was then deposited onto the light-emitting layer. This material was also evaporated from a graphite boat.

f) On top of the $Alq_3$ layer was deposited a 220 nm cathode formed of a 10:1 volume ratio of Mg and Ag.

The above sequence completed the deposition of the EL device. The device was then hermetically packaged in a dry glove box for protection against ambient environment.

TABLE 3a

Components used in the LEL.

| Device | PH-10 Wt % | NPB Wt % | Inv-2 Wt % |
|---|---|---|---|
| 3-1 | 83 | 15 | 2 |
| 3-2 | 81 | 15 | 4 |
| 3-3 | 76 | 20 | 4 |
| 3-4 | 66 | 30 | 4 |
| 3-5 | 74 | 20 | 6 |
| 3-6 | 94 | 0 | 6 |

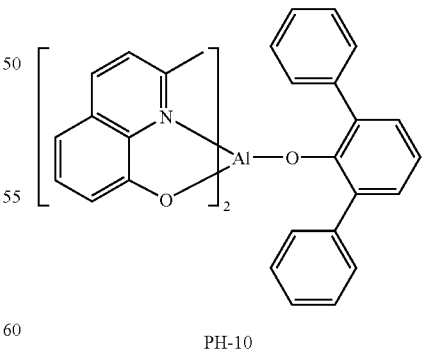

PH-10

The cells thus formed were tested at 0.5 mA/cm$^2$ constant current for efficiency in the form of luminance yield (Cd/A) and radiant yield (W/A). Testing was also determined the output color reported in CIEx, CIEy coordinates and drive voltage. The results are listed in Table 3b.

The stability of the devices was also measured by operating the devices for 474 hrs at a current density of 20 mA/cm². The percent of luminance remaining after this time period is listed in Table 3b.

TABLE 3b

Testing data for Devices 3-1 through 3-6.

| Device | Color CIEx,y | Luminance Yield (cd/A)[1] | Drive Voltage (V)[1] | Emission $\lambda_{max}$ (nm) | Radiant Yield | Stability[2] (%) |
|---|---|---|---|---|---|---|
| 3-1 | 0.661,0.323 | 5.27 | 7.2 | 636 | 0.136 | 87 |
| 3-2 | 0.673,0.319 | 4.50 | 7.2 | 639 | 0.131 | 86 |
| 3-3 | 0.673,0.318 | 4.68 | 6.3 | 639 | 0.135 | 87 |
| 3-4 | 0.674,0.316 | 5.07 | 5.6 | 638 | 0.142 | 84 |
| 3-5 | 0.678,0.315 | 4.25 | 6.4 | 641 | 0.135 | 87 |
| 3-6 | 0.612,0.362 | 2.52 | 8.5 | 645 | 0.066 | 82 |

[1]Measured at 0.5 mA/cm² constant current.
[2]Percent luminance remaining after 474 hours of operation.

It can be seen from Table 3b, that the inventive devices offer high luminance and excellent stability. In addition, if one compares Devices 3-1 through 3-5, which have a host material that is a mixture of PH-10 and NPB, with Device 3-6 which has only a single host (PH-10), one can see that the mixed host in combination with the dopant of Formula (1) offers a significant improvement in luminance yield, efficiency, and stability as well as reduced drive voltage.

The invention has been described in detail with particular reference to certain preferred embodiments thereof, but it will be understood that variations and modifications can be effected within the spirit and scope of the invention.

The patents and other publications referred to are incorporated herein in their entirety.

PARTS LIST

101 Substrate
103 Anode
105 Hole-Injecting layer (HIL)
107 Hole-Transporting layer (HTL)
109 Light-Emitting layer (LEL)
110 Hole-Blocking Layer (HBL)
111 Electron-Transporting layer (ETL)
113 Cathode
150 Voltage/Current Source
160 Electrical Connectors

The invention claimed is:

1. An OLED device comprising a cathode, an anode, and located therebetween a light-emitting layer containing a host material and a tris-C^N-cyclometallated complex represented by Formula (2d):

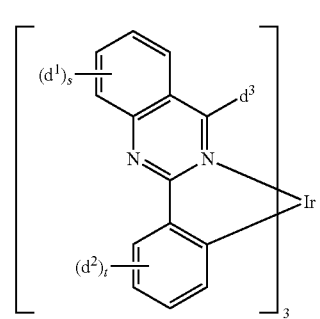

(2d)

wherein:
each $d^1$ represents an independently selected substituent and s is 0-4;
each $d^2$ represents an independently selected substituent and t is 0-4; and
$d^3$ represents hydrogen or a substituent.

2. A tris-C^N-cyclometallated complex is represented by Formula (2d):

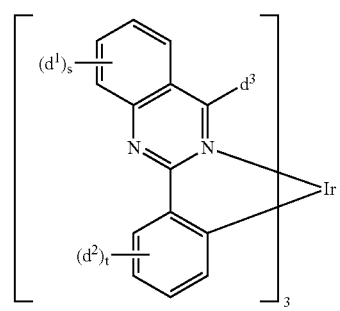

(2d)

wherein:
each $d^1$ represents an independently selected substituent and s is 0-4;
each $d^2$ represents an independently selected substituent and t is 0-4; and
$d^3$ represents hydrogen or a substituent.

3. The device of claim 1 wherein the host material comprises an aluminum complex.

4. The device of claim 3 wherein the host comprises a material of Formula (4):

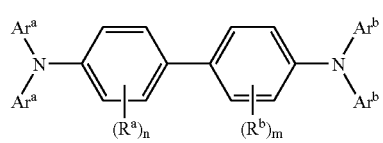

(4)

wherein:
each $Ar^a$ and each $Ar^b$ may be the same or different and each independently represents an aromatic group;
each $R^a$ and each $R^b$ may be the same or different and each independently represents a substituent group; and
n and m independently are 0-4.

5. The device of claim 1 wherein the host material comprises a material of Formula (3):

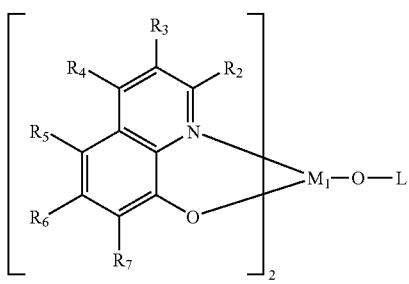

(3)

wherein:
M₁ represents Al or Ga;
R₂ through R₇ each independently represent hydrogen or a substituent group, and
L represents an aromatic group.

6. The device of claim 1 wherein the host comprises a triaryl amine.

7. The device of claim 1 wherein the host material comprises an aluminum complex and a triaryl amine.

8. The device of claim 1 wherein the host material comprises a carbazole biphenyl compound.

9. The device of claim 8 wherein the host material comprises 4,4'-N,N'-dicarbazole-biphenyl.

10. The tris-C^N-cyclometallated complex

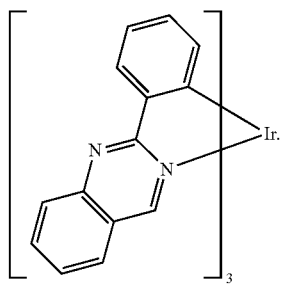

(Inv-1)

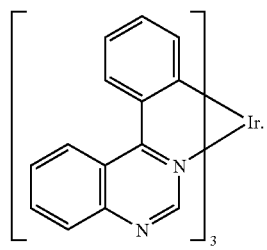

(Inv-2)

* * * * *

UNITED STATES PATENT AND TRADEMARK OFFICE
CERTIFICATE OF CORRECTION

| | | |
|---|---|---|
| PATENT NO. | : 9,040,170 B2 | Page 1 of 1 |
| APPLICATION NO. | : 11/289023 | |
| DATED | : May 26, 2015 | |
| INVENTOR(S) | : Joseph C. Deaton and Barbara B. Lussier | |

It is certified that error appears in the above-identified patent and that said Letters Patent is hereby corrected as shown below:

IN THE CLAIMS:

In claim 10, please remove the text "Inv-2" and the accompanying structure at column 54, lines 15-24. Claim 10 should appear as shown below.

--10. The tris-C^N-cyclometallated complex

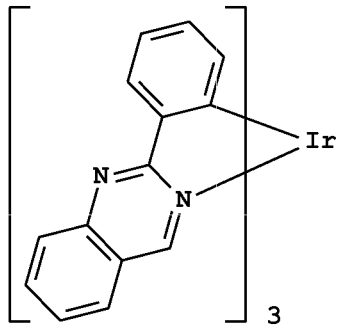

(Inv-1). --

Signed and Sealed this
Fifth Day of July, 2016

Michelle K. Lee
*Director of the United States Patent and Trademark Office*